(12) United States Patent
Paek et al.

(10) Patent No.: US 11,634,371 B2
(45) Date of Patent: Apr. 25, 2023

(54) ADVANCED ADSORPTIVE SEPARATION PROCESSES FOR MOLECULAR CLASS SEPARATION

(71) Applicant: ExxonMobil Technology and Engineering Company, Annandale, NJ (US)

(72) Inventors: Changyub Paek, Bridgewater, NJ (US); Randall D. Partridge, Califon, NJ (US); Yogesh V. Joshi, Bridgewater, NJ (US); Jayashree Kalyanaraman, Clinton, NJ (US); Joseph M. Falkowski, Hampton, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/457,731

(22) Filed: Dec. 6, 2021

(65) Prior Publication Data
US 2022/0177393 A1    Jun. 9, 2022

Related U.S. Application Data

(60) Provisional application No. 63/123,086, filed on Dec. 9, 2020.

(51) Int. Cl.
*C07C 7/13* (2006.01)
*B01D 15/08* (2006.01)
(Continued)

(52) U.S. Cl.
CPC ............... *C07C 7/13* (2013.01); *B01D 15/08* (2013.01); *B01J 20/103* (2013.01); *B01J 20/18* (2013.01);
(Continued)

(58) Field of Classification Search
CPC .. C07C 7/005; C07C 7/12; C07C 7/13; B01D 15/08; B01J 20/103; B01J 20/12;
(Continued)

(56) References Cited

U.S. PATENT DOCUMENTS 2,856,444 A   10/1958   Pollock
2,985,589 A    5/1961   Broughton et al.
(Continued)

FOREIGN PATENT DOCUMENTS

WO    2017048378 A1    3/2017

OTHER PUBLICATIONS

Kramer et al. ("Influence of group II & III base oil composition on VI and oxidation stability." NLGI spokesman 63.10 (2000): 20-39) (Year: 2000).*
(Continued)

*Primary Examiner* — In Suk C Bullock
*Assistant Examiner* — Jason Y Chong
(74) *Attorney, Agent, or Firm* — Shook, Hardy & Bacon L.L.P.

(57) ABSTRACT

A method for separating classes of hydrocarbon compounds from a feed stream including a hydrocarbon mixture is disclosed. The method includes the steps of passing a feed stream through a plurality of separation units arranged in a series in any order, wherein each separation unit has an adsorbent material; and separating classes of hydrocarbon compounds from the feed stream. When one of the plurality of separation units comprises an adsorbent material that is a metal organic framework selected from a zirconium, hafnium, cerium, or titanium-based metal organic framework, then another plurality of separation units includes an adsorption material that is different from the metal organic framework. The method is conducted in a liquid phase. The method can also use a single separation unit with a continu-
(Continued)

ous cyclic bed apparatus. The method can be combined with refining and downstream processes.

23 Claims, 19 Drawing Sheets

(51) Int. Cl.
  *C07C 7/12* (2006.01)
  *B01J 20/22* (2006.01)
  *B01J 20/10* (2006.01)
  *B01J 20/18* (2006.01)
  *C07C 7/00* (2006.01)

(52) U.S. Cl.
  CPC ............ *B01J 20/226* (2013.01); *C07C 7/005* (2013.01); *C07C 7/12* (2013.01); *B01J 2220/603* (2013.01)

(58) Field of Classification Search
  CPC .... B01J 20/18; B01J 20/226; B01J 2220/603; C10G 25/003; C10G 25/03
  See application file for complete search history.

(56) References Cited

U.S. PATENT DOCUMENTS

| | | | |
|---|---|---|---|
| 3,510,423 | A | 5/1970 | Neuzil et al. |
| 3,686,342 | A | 8/1972 | Neuzil |
| 5,750,820 | A | 5/1998 | Wei |
| 9,956,541 | B2 | 5/2018 | Weigel et al. |
| 11,377,605 | B2 | 7/2022 | Partridge et al. |
| 2008/0036913 | A1 | 2/2008 | Yeh et al. |
| 2016/0340181 | A1* | 11/2016 | Ornstein ............... C01B 3/0015 |
| 2018/0079970 | A1 | 3/2018 | Chawla et al. |
| 2021/0062584 | A1 | 3/2021 | Wang et al. |

OTHER PUBLICATIONS

Thommes, M. et al., "Physisorption of gases, with special reference to the evaluation of surface area and pore size distribution (IUPAC Technical Report)," Pure Appl. Chem., 87(9-10): 1051-1069 (2015).
Maes, M et al., "Separation of C5-Hydrocarbons on Microporous Materials: Complementary Performance of MOFs and Zeolites", J. Am. Chem. Soc., Oct. 16, 2009, vol. 132, No. 7. pp. 2284-2292.
PCT/US2021/072750 International Search Report and Written Opinion dated Mar. 18, 2022.
Li, et al., Template-Free Self-Assembly of Mesoporous Organosilicas, Chem. Mater. 2018, 30, 7, 2218-2228.

* cited by examiner

ADVANCED ADSORPTIVE SEPARATION PROCESSES FOR MOLECULAR CLASS SEPARATION

CROSS-REFERENCE TO RELATED APPLICATIONS

This application claims the benefit of U.S. Provisional Application No. 63/123,086, filed on Dec. 9, 2020, the entire contents of which are incorporated herein by reference.

FIELD

The present invention relates to a liquid phase adsorptive process for separation of feed streams by molecular class. The feed streams may be refinery streams and comprise a hydrocarbon mixture.

BACKGROUND

A petroleum refinery has conventionally been built around thermal phase change-based separation processes with atmospheric and vacuum distillation being at the front end of the refinery. In the current state of the art, distillation is the cornerstone of all refining processes. So much so that refining streams and downstream processes and products are often designed for and defined in terms of boiling point ranges. In a typical distillation process, desalted crude is first fed to an atmospheric and then a vacuum distillation column. Distillation separates based on differences in relative volatility involving phase change and vapor-liquid equilibrium. In other words, the crude oil is heated so that each fraction evaporates or boils and then condenses in its own compartment of the distillation column, which is not thermally efficient.

Distillation cuts by boiling points include a mixture of different types of molecules, which complicates downstream process designs including process configuration, catalysts selection, and reaction conditions. Molecules other than the desired molecules or primary reactants could be downgraded by nonselective side reactions that would ultimately devalue initial feed molecules. For example, paraffinic and iso-paraffinic molecules in a reformer feed undergo cracking, which is one of undesired reactions occurring during reforming. At the same time, the feeds with these undesired molecules would reduce the unit throughput due to hydrodynamic and thermal limitations.

SUMMARY

Aspects of the disclosure herein refer to a liquid phase method that provides a molecular class separation of a feed stream comprising a hydrocarbon mixture by applying advanced adsorptive separation instead of conventional boiling point separation like distillation.

In one aspect, the present invention is a method comprising the steps of: passing a feed stream comprising a hydrocarbon mixture through a plurality of separation units arranged in a series in any order, wherein each separation unit has an adsorbent material; and separating classes of hydrocarbon compounds from the feed stream. One of the plurality of separation units comprises an adsorbent material that is a metal organic framework selected from a zirconium, hafnium, cerium, or titanium-based metal organic framework. Another of the plurality of separation units has an adsorption material that is different from the metal organic framework. The adsorptive separation method is conducted in a liquid phase.

In some embodiments, another of the plurality of separation units comprises an adsorbent material that is independently selected from a porous silica, a small pore zeolite, a medium pore zeolite, or a large pore zeolite.

In some embodiments, the hydrocarbon mixture in the feed stream comprises one or more n-paraffins, one or more iso-paraffins, one or more one-ring cycloparaffins, one or more multi-ring cycloparaffins, and one or more aromatic compounds. In some embodiments, the feed stream is a refinery stream.

In some embodiments, the separation unit that comprises an adsorbent material that is the porous silica or the large pore zeolite generates an extract stream comprising the one or more aromatic compounds.

In some embodiments, the separation unit that comprises an adsorbent material that is the metal organic framework generates an extract stream comprising the one or more one-ring cycloparaffins and the one or more multi-ring cycloparaffins.

In some embodiments, the separation unit that comprises an adsorbent material that is the small pore zeolite or a medium pore zeolite generates an extract stream comprising the one or more n-paraffins.

In some embodiments, each of the plurality of separation units is independently selected from a fixed bed apparatus, a moving bed apparatus, simulated moving bed apparatus, a temperature swing adsorption apparatus, or a concentration swing adsorption apparatus. In some embodiments, the method further comprises desorbing using at least one solvent. In some embodiments, the solvent comprises a saturated hydrocarbon, olefinic hydrocarbon, an aromatic hydrocarbon, or mixtures thereof.

In another aspect, the method of the present invention further comprises the step of generating one or more extract streams, wherein each extract stream comprises a class of hydrocarbon compounds from the feed stream, and one or more raffinate streams comprising the rest of the classes of hydrocarbon compounds from the feed stream.

In some embodiments, the method of the present invention comprises a further step of supplying the one or more extract streams and the one or more raffinate streams to a conversion unit or a blending unit. In some embodiments, a first extract stream or a first raffinate stream is supplied to a conversion unit and a second extract stream or a second raffinate stream is distilled prior to supplying to a conversion unit or a blending unit. In some embodiments, the conversion unit is selected from a cracking unit, a reforming unit, or a synthesis unit.

In another aspect, the method of the present invention comprises the steps of: passing a feed stream comprising a hydrocarbon mixture through a separation unit with an adsorbent material comprising a metal organic framework selected from a zirconium, hafnium, cerium, or titanium-based metal organic framework; and separating with a simulated moving bed apparatus or a true moving bed apparatus (SMB/TMB) classes of hydrocarbon compounds from the feed stream, wherein the method is conducted in a liquid phase. In some embodiments, the SMB/TMB comprises a binary or a ternary outlet.

BRIEF DESCRIPTION OF DRAWINGS

FIG. 14(*b*) depicts reconstructed chromatogram after running the feed composition of FIG. 14(*a*) through a packed bed of mesoporous organo silica (MOS); FIG. 14(*c*) depicts 2DGC chromatogram of one of the paraffin fractions obtained by the process of FIG. 14(*b*); FIG. 14(*d*) depicts 2DGC chromatogram of one of the aromatic fractions obtained by the process of FIG. 14(*b*).

FIG. 16(*a*) depicts overlays of individual breakthrough curves of components; FIG. 16(*b*) depicts overlays of breakthrough curves by a compound class, i.e. n-paraffins, iso-paraffins, cycloparaffins (normalized by each component's initial concentration).

DETAILED DESCRIPTION

Figure 1:
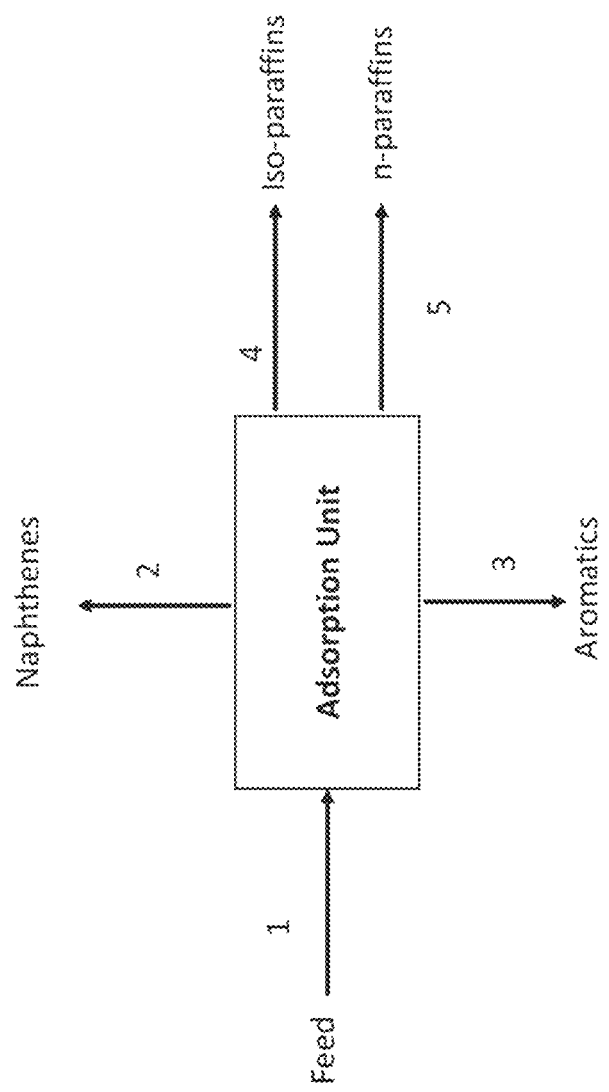
FIG. 1 is a flow diagram of a process for separating classes of hydrocarbon compounds from a feed stream according to one embodiment of the present disclosure.

The disclosure herein refers to a liquid phase method for separating classes of hydrocarbon compounds from a feed stream comprising a hydrocarbon mixture. In one embodiment, the feed stream is a refinery stream. In one embodiment, the feed stream is a fractionated cut that may come from a main distillation tower of crude oil. The present method applies advanced adsorptive separation instead of conventional boiling point separation like distillation.

As used herein, and unless otherwise specified, the term "feed stream" is intended to indicate a stream which comprises the feed material and which is charged to the bed of adsorbent material for the purpose of recovering the extract component. The feed stream will comprise one or more extract components and one or more raffinate components. An extract component is a chemical compound which is preferentially adsorbed by the adsorbent material which is being used as compared to a raffinate component. The process of generating extract and raffinate components (for example, in extract and raffinate streams, respectively) with compositions that are different than the composition of the feed stream is referred to herein as separation.

As used herein, and unless otherwise specified, the term "extract stream" refers to a stream which contains extract components that were originally contained in the feed stream and that have been desorbed from the bed of adsorbent material by the desorbent stream. The extract stream is basically the adsorbed or strongly adsorbed components of the feed stream plus desorbent components which are picked up during passage through the adsorption zone. The composition of the extract stream as it leaves the bed of adsorbent material will normally vary with time, and depending on conditions this composition can range from about 0 to about 100 mole percent extract components to about 100 to about 0 mole percent desorbent components.

As used herein, and unless otherwise specified, the term "raffinate stream" is intended to indicate a stream originating at the bed of adsorbent material and which contains the majority of the raffinate components of the feed stream. The raffinate stream is basically the non-adsorbed or weakly adsorbed components of the feed stream plus desorbent components which are picked up during passage through the adsorption zone. The composition of the raffinate stream as it leaves the bed of adsorbent material will also vary with time from a high percentage of desorbent components to a high percentage of raffinate components.

As used herein, and unless otherwise specified, the term "class" or "molecular class" of hydrocarbon compounds refers to different types of hydrocarbons, such as normal or linear paraffins, branched paraffins or iso-paraffins, cycloparaffins, and aromatic hydrocarbons.

The feed stream can comprise any combination of hydrocarbons. In some embodiments, the hydrocarbon mixture of the feed stream comprises one or more normal paraffins (i.e., n-paraffins), one or more branched paraffins (i.e., iso-paraffins), one or more one-ring cycloparaffins, one or more multi-ring cycloparaffins, and one or more aromatic hydrocarbons, or combinations thereof.

In some embodiments, the hydrocarbon mixture can include at least five carbon atoms per molecule. In some embodiments, the hydrocarbon mixture can include five to twenty-five carbon atoms per molecule. In some embodiments, the hydrocarbon mixture can include up to about 95% n-paraffins. In some embodiments, n-paraffins that can be present in the hydrocarbon mixture have at least five carbon atoms per molecule. In some embodiments, n-paraffins that can be present in the hydrocarbon mixture have five to twenty-five carbon atoms per molecule. In some embodiments, the hydrocarbon mixture can include up to about 95% iso-paraffins. In some embodiments, the hydrocarbon mixture can include up to about 95% aromatic hydrocarbons. In some embodiments, the hydrocarbon mixture can include up to about 95% cycloparaffins.

Some of the components included in the hydrocarbon mixture can be substituted or unsubstituted. In some embodiments, the hydrocarbon mixture comprises one or more n-paraffins, one or more iso-paraffins, one or more substituted or unsubstituted aromatic hydrocarbons, one or more substituted or unsubstituted cycloparaffins, or combinations thereof.

In some embodiments, the cycloparaffins in the hydrocarbon mixture have at least five carbon atoms per molecule. In some embodiments, the cycloparaffins in the hydrocarbon mixture have five to twenty-five carbon atoms per molecule. In a preferred embodiment, cycloparaffins (i.e., naphthenes) include one or more one-ring cycloparaffins and one or more multi-ring cycloparaffins. Non-limiting examples of cycloparaffins that can be present in the hydrocarbon mixture include, e.g., cyclohexane, decalin, n-octadecyl-cyclohexane ($C_{24}H_{48}$), or combinations thereof. Non-limiting examples of the one or more multi-ring cycloparaffins that can be present in the hydrocarbon mixture include, e.g., one or more two-ring cycloparaffins. In some embodiments, the cycloparaffins comprise decalins. Non-limiting examples of decalins include, e.g., substituted or unsubstituted decalins, branched or unbranched decalins. In one example, the decalin is methyl decalin. In another example, the decalin is cis-/trans-decalin.

The aromatic compound can be a single ring aromatic and/or a multi-ring aromatic (e.g., 2 or more rings). Examples of single ring aromatic compounds include, but are not limited to, benzene, toluene, ethylbenzene, xylenes and propylbenzene. Examples of double ring aromatic compounds include, but are not limited to tetralin, naphthalene, and biphenyl.

The feed streams which may be suitable for use in the methods described herein include fractional cuts that may come from a main distillation tower of crude oil, input feeds that can be generated as a product or side-product from a previous type of hydroprocessing, such as hydrocracking for fuels. Such feed streams can include hydrocarbon fluids, gasoline, diesel, kerosene feed streams, and mixtures of these materials. Such feed streams can also include other distillate feed streams such as light to heavy distillates including raw virgin distillates. Diesel boiling range feed streams include feed streams which boil in the range of 480-660° F. Kerosene boiling range feed streams include feed streams which boil in the range of 350-617° F.

The method of separation of the present disclosure uses advanced adsorptive separation instead of conventional boiling point separation like distillation. As used herein, and unless otherwise specified, the term "adsorption" includes physisorption and chemisorption, onto a solid material and combinations thereof. The feed stream is passed through a plurality of separation units arranged in a series in any order. Each of the plurality of separation units comprises an adsorbent material. The adsorbent material can be varied depending on the hydrocarbons that need to be separated from the feed stream.

On passing the feed stream through a separation unit, the feed stream contacts the adsorbent material in the separation unit. The adsorbent material may be packed into one or more columns and/or one or more adsorbent beds. For example, the feed stream can contact a bed of an adsorbent material in a down flow direction (e.g., flow directed by gravity). In non-limiting embodiments, the adsorbent can be present in a column and the feed stream can be applied to a column containing the adsorbent material. In some embodiments, the bed of an adsorbent can be contained within a liquid chromatography column. The liquid chromatography column can be, for example, a low-pressure or a high performance liquid chromatography (HPLC) column. In one example, the adsorbent material can be contained within a HPLC column. In some embodiments, the separation unit is selected from a fixed bed apparatus, a moving bed apparatus, a simulated moving bed apparatus, a temperature swing adsorption apparatus, or a concentration swing adsorption apparatus.

The adsorbent material in each of the plurality of separation units is typically different from each other. Each adsorbent material is selected based on its preferential adsorption of a particular class of hydrocarbon. When the feed stream comprising a hydrocarbon mixture comes in contact with the adsorbent material, that particular class of hydrocarbons is preferentially adsorbed, which can be separated from the hydrocarbon mixture as an extract stream that is a pure, a substantially pure, or rich in that particular class of hydrocarbon. The raffinate stream can be fed to another of the plurality of separation units that has a different adsorbent material which preferentially adsorbs a different class of hydrocarbon, and hence, separates that different class of hydrocarbon as an extract stream that is a pure, a substantially pure, or rich in that different class of hydrocarbon. The present method can be customized to use specific adsorbent materials in a specific order based on the components in a hydrocarbon mixture that need to be separated by hydrocarbon class.

One embodiment of a method for separating a feed stream comprising a hydrocarbon mixture into classes of hydrocarbon compounds is illustrated in FIG. 1, in which a feed comprising one or more n-paraffins, one or more iso-paraffins, one or more one-ring cycloparaffins, one or more multi-ring cycloparaffins, and one or more aromatic compounds is fed via line 1 to an "Adsorption Unit". The Adsorption Unit comprises a plurality of separation units arranged in a series in any order. Each separation unit comprises a different adsorbent which preferentially adsorbs a different hydrocarbon compound. For example, one of the plurality of separation units comprises an adsorbent that preferentially adsorbs naphthenes, which exits the Adsorption Unit as a stream rich in naphthenes via line 2. Another of the plurality of separation units comprises an adsorbent that preferentially adsorbs aromatics, which exits the Adsorption Unit as a stream rich in aromatics via line 3. Yet another of the plurality of separation units comprises an adsorbent that preferentially adsorbs iso-paraffins, which exits the adsorption unit as a stream rich in iso-paraffins via line 4. The remaining stream that is depleted of naphthenes, aromatics, and iso-paraffins, and which comprises n-paraffins, exits the Adsorption Unit via line 5.

Figure 2:
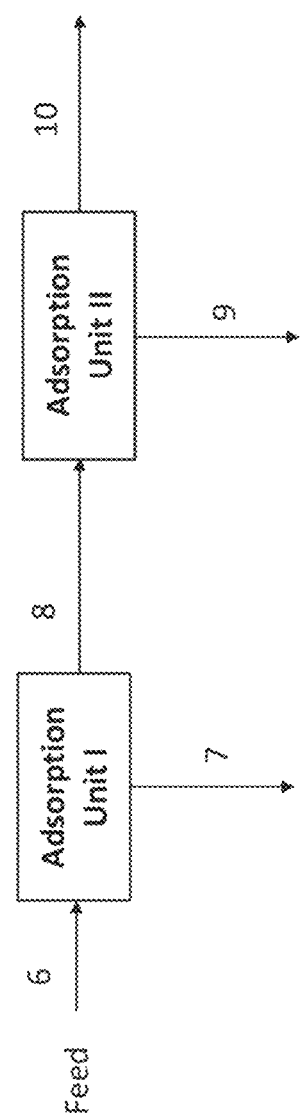
FIG. 2 is a flow diagram of a process for separating classes of hydrocarbon compounds from a feed stream according to one embodiment of the present disclosure.

The plurality of separation units are arranged in a series in any order. As illustrated in FIG. 2, a feed comprising, for example, one or more n-paraffins, one or more iso-paraffins, one or more one-ring cycloparaffins, one or more multi-ring cycloparaffins, and one or more aromatic compounds is fed via line 6 to an "Adsorption Unit I". Adsorption Unit I comprises an adsorbent which preferentially adsorbs a particular hydrocarbon compound. For example, if the Adsorption Unit I comprises an adsorbent which preferentially adsorbs aromatic compounds, then aromatic compounds exit Adsorption Unit I as a stream rich in aromatic compounds through line 7. The remaining aromatic compounds depleted stream, which comprises one or more n-paraffins, one or more iso-paraffins, and one or more naphthenes, exits via line 8 and is subsequently fed to a second separation unit labeled as "Adsorption Unit II," which is connected in series to Adsorption Unit I. The Adsorption Unit II comprises an adsorbent that preferentially adsorbs, for example, naphthenes, which exit the Adsorption Unit II as a stream rich in naphthenesvia line 9. The one or more n-paraffins and the one or more iso-paraffins exit the Adsorption Unit II via line 10.

The method of separation of the present disclosure further comprises desorbing using a solvent (i.e., desorbent). The hydrocarbon mixture can contact the adsorbent material in the presence of the solvent. In some embodiments, the solvent can contact the adsorbent material prior to and/or after the contact of the hydrocarbon mixture with the adsorbent material. In alternate embodiments, the hydrocarbon mixture can contact the adsorbent material concomitantly with the solvent.

In some embodiments, the solvent is a non-polar solvent. In some embodiments, the solvent is a saturated hydrocarbon, an aromatic hydrocarbon, or mixtures thereof. Non-limiting examples of the solvent include, e.g., iso-octane, $C_4$-$C_8$ n-paraffin, $C_4$-$C_8$ iso-paraffin, $C_{11}$-$C_{18}$ n-paraffin, $C_{11}$-$C_{18}$ iso-paraffin, n-hexane, cyclohexane, toluene, benzene, $CO_2$, ammonia, or mixtures thereof.

In some embodiments, the solvent can include one or more lower paraffins. A "lower paraffin," as used herein, includes a paraffin that has one to eight carbon atoms. Non-limiting examples of solvents for use with the adsorbent material include $C_4$-$C_8$ n-paraffin, n-hexane, iso-hexane, heptane, iso-heptane, octane, iso-octane or combinations thereof. In one example, the solvent can include iso-octane. In an alternate example, the solvent can include hexane and iso-octane. In an alternate example, the solvent can include hexane and iso-octane, with the amount of hexane in the combination being about 0-99% of the total.

As embodied herein, the linear flow velocity of the hydrocarbon mixture solution through the adsorbent material can be from about 0.3 cm/min to about 30.0 cm/min, e.g., from about 6.0 cm/min to about 30.0 cm/min, from about 6.0 cm/min to about 24.0 cm/min, from about 6.0 cm/min to about 18.0 cm/min or from about 6.0 cm/min to about 12.0 cm/min. In one example, the flow rate of the hydrocarbon sample through the adsorbent material can be about 2.4 cm/min.

In some embodiments, the method is performed at a temperature from about 25° C. to about 250° C. The stability of the metal-organic framework or the other adsorbent material will determine higher end temperature. In one example, the temperature can be about 150° C. In some embodiments, the process is performed at a pressure of about 1 bar to about 100 bar. In one example, the pressure can be 50 bar or high enough to maintain liquid phase for a given composition and pressure.

The adsorbent material in each of the plurality of separation units is independently selected from a metal-organic framework (MOF) material, a porous silica, a small pore zeolite, a medium pore zeolite, or a large pore zeolite.

In some embodiments, the adsorbent material of the present invention is a MOF material. In some embodiments, the MOFs are constructed from transition or rare earth metal or their oxide ions as nodes and multidentate organic ligands containing O- or N-donors as linkers. In some embodiments, the MOF is zirconium, hafnium, cerium, or titanium-based MOF. In one example, the MOF is a zirconium-based MOF. In a preferred embodiment, the MOF adsorbent material is the MOF disclosed in U.S. Provisional Application No. 62/915,663, which is incorporated by reference herein. This MOF adsorbent material preferentially adsorbs the one or more one-ring cycloparaffins and the one or more multi-ring cycloparaffins from a hydrocarbon mixture that comprises n-paraffins, one or more iso-paraffins, one or more one-ring cycloparaffins, one or more multi-ring cycloparaffins. In some embodiments, the metal organic framework adsorbent material preferentially adsorbs hydrocarbons in the order of the one or more one-ring cycloparaffins and the one or more multi-ring cycloparaffins, the one or more aromatics, the one or more iso-paraffins, followed by the one or more n-paraffins. In some embodiments, the metal organic framework adsorbent material preferentially adsorbs one or more aromatic compounds as strongly as or even more strongly than the one or more one-ring cycloparaffins and the one or more multi-ring cycloparaffins.

In contrast to the commercially available MOFs that can be nearly free of defects, the MOF adsorbent materials used herein contain defects, which provide the preferential separation properties noted above. In some embodiments, the level of defect in an MOF can be inferred from micropore volume as measured by nitrogen adsorption at 77° K, as described in Thommes, M. et al., "Physisorption of gases, with special reference to the evaluation of surface area and pore size distribution (IUPAC Technical Report)," Pure Appl. Chem., 87(9-10):1051-1069 (2015), which is incorporated by reference herein. For a commercial MOF material, such as UiO-66 ($Zr_6(OH)_4O_4(BDC)_6$, wherein "BDC" is benzene-1,4-dicarboxylate), which is sold by ProfMOF as commercial UiO-66, the measured micropore volume of 0.38 cc/g represents a lower bound. Accordingly, when this commercial material is modified for the present method, it needs to have a measured micropore volume of greater than 0.38 cc/g.

In some embodiments, the level of defect in an MOF can be inferred from the weight of residual inorganic solids as measured by thermogravimetric analysis. In this method, the weight of the sample of MOF remaining after combusting the sample is compared to the dry weight of the sample of MOF as measured at 300° C. Specifically, the residual inorganic mass is obtained by heating a sample of the MOF in air flowing at a rate between about 3° C./min and 10° C./min. The weight of the sample of MOF as measured at temperatures above 600° C. is compared to the dry mass of the sample of MOF as measured at 300° C. Residual inorganic mass can then be described as $Mass_{600° C.}/Mass_{300° C.}$. For a commercial material obtained from ProfMOF (UiO-66-BDC), % inorganic solids measured by this method was about 45 wt %. Accordingly, when this commercial material is modified for the present method, it needs to have a residual inorganic mass after combustion of greater than about 45 wt % of that of the dry sample at 300°

C. In some embodiments, the Zr-MOF suitable for the present method can be represented by a general formula $Zr_6O_4(OH)_4BDC_{(6-x)}$, wherein BDC refers to benzene-1,4-dicarboxylate, and wherein x is greater than 0.5 as determined by residual inorganic mass after combustion.

As disclosed in U.S. Provisional Application No. 62/915,663, the above controlled defect ridden UiO-66 Zr-MOF exhibited an X-ray diffraction pattern containing peaks at d-spacings of about 11.98 Å, 10.37 Å, 7.32 Å, 6.24 Å, 5.98 Å, and 5.18 Å. The adsorbent material comprising the above controlled defect ridden UiO-66 Zr-MOF also exhibited such an X-ray diffraction pattern.

In some embodiments, the adsorbent material of the present method comprises the MOF and a binder for commercial packing material preparation. The binder can be an inorganic binder (such as alumina or silica), or the binder can be an organic binder (such as an organic polymer). In some embodiments, the adsorbent material comprises about 95% MOF and about 5% binder. Alternatively, the adsorbent material comprises about 90% MOF and about 10% binder. Alternatively, the adsorbent material comprises about 85% MOF and about 15% binder.

In some embodiments, the adsorbent material of the present invention is a porous silica. In some embodiments, the porous silica is silica gel, mesoporous organo silica (MOS), or clay. As used herein, and unless otherwise specified, the term "mesoporous" refers to solid materials having pores that have a diameter within the range of from about 2 nm to about 50 nm. As used herein, and unless otherwise specified, the term "organosilica" refers to an organosiloxane compound that comprises one or more organic groups bound to two or more Si atoms.

The porous silica preferentially adsorbs aromatic compounds from a hydrocarbon mixture that comprises n-paraffins, one or more iso-paraffins, one or more one-ring cycloparaffins, one or more multi-ring cycloparaffins, and one or more aromatic compounds.

In some embodiments, the adsorbent material of the present invention is a small pore zeolite, a medium pore zeolite, or a large pore zeolite.

A small pore size zeolite has a maximum effective pore size from about 3 Å to about 5.0 Å. In some embodiments, the small pore zeolite has a crystal size of less than 5 μm.

In one embodiment, the small pore zeolite has an 8 membered ring structure. Non-limiting examples of the structure type of the small pore 8 membered ring zeolite include, e.g., ABW, AEI, AFX, ANA, ATT, BCT, BIK, BRE, CAS, CDO, CHA, DDR, EAB, EDI, EEI, EPI, ERI, ESV, GIS, GOO, IHW, ITE, JBW, KFI, LEV, LTA, LTJ, LTN, MER, MON, MTF, MWF, NSI, PAU, PHI, RHO, RTH, SAS, SFW, THO, TSC, UFI, YUG, ETL, IFY, ITW, RTE, RWR, or combinations thereof [using the nomenclature of the International Union of Pure and Applied Chemistry (IUPAC) Commission of Zeolite Nomenclature].

In some embodiments, the small pore zeolite comprises a structure type LTA, ZK-4, CHA, RHO, or combinations thereof. In one example, the small pore zeolite comprises zeolite Type A structure, for example, zeolite 5A. Non-limiting examples of the small pore zeolite include, e.g., ZK-4, ZK-5, zeolite A, or zeolite T. Non-limiting examples of small pore zeolites can also be shown with reference to the general framework to which they belong, e.g., LTA (ZK-4, zeolite A), or KFI (ZK-5), zeolite A, or zeolite T.

The small pore zeolite preferentially adsorbs n-paraffins from a hydrocarbon mixture that comprises n-paraffins, one or more iso-paraffins, one or more one-ring cycloparaffins, one or more multi-ring cycloparaffins, and one or more aromatic compounds.

A medium pore size has a maximum effective pore size of from about 5 Å to about 6.8 Å. In one embodiment, the medium pore zeolite has a 10 membered ring structure. Non-limiting examples of the structure type of the medium pore 10 membered ring zeolite include, e.g., MFI, MEL, EUO, MTT, MRE, HEU, FER, and TON. Non-limiting examples of the medium pore zeolite include, e.g., ZSM-5, ZSM-11, ZSM-22, ZSM-23, ZSM-35, or ZSM-48. Non-limiting examples of medium pore zeolites can also be shown with reference to the general framework to which they belong, e.g., MFI (ZSM-5), MEL (ZSM-11), TON (ZSM-22), MTT (ZSM-23), FER (ZSM-35), or MRE (ZSM-48).

The medium pore zeolite preferentially adsorbs n-paraffins from a hydrocarbon mixture that comprises n-paraffins, one or more iso-paraffins, one or more one-ring cycloparaffins, one or more multi-ring cycloparaffins, and one or more aromatic compounds.

A large pore zeolite has a maximum effective pore size of >7 Å. In one embodiment, the large pore zeolite has a 12 membered or larger ring structure. Non-limiting examples of the structure type of the large pore 12 membered ring zeolite include, e.g., MWW, LTL, MOR, MAZ, MEI, FAU, or EMT. Non-limiting examples of the large pore zeolite include, e.g., Mordenite, zeolite 13X, zeolite X, zeolite Y, Siliceous Y, ZSM-3, ZSM-4, ZSM-12, ZSM-18, ZSM-20, Beta, or zeolite L. Non-limiting examples of large pore zeolites can also be shown with reference to the general framework to which they belong, e.g., MWW (MCM-22), MOR (Mordenite), FAU (zeolite 13X, zeolite X, zeolite Y, Siliceous Y), EMT (ZSM-3), MAS (ZSM-4), MTW (ZSM-12), MEI (ZSM-18), EMT (ZSM-20), BEA (Beta), LTL (zeolite L), or DON (UTD-1).

The large pore zeolite preferentially adsorbs aromatic compounds from a hydrocarbon mixture that comprises n-paraffins, one or more iso-paraffins, one or more one-ring cycloparaffins, one or more multi-ring cycloparaffins, and one or more aromatic compounds.

In some embodiments, the method of the present invention further comprises the step of generating: one or more extract streams, with each extract stream comprising a class of hydrocarbon compounds from the feed stream, and one or more raffinate streams comprising the rest of the classes of hydrocarbon compounds from the feed stream.

In some embodiments, the method for separating classes of hydrocarbon compounds from a feed stream comprises the steps of: passing a feed stream comprising a hydrocarbon mixture comprising one or more n-paraffins, one or more iso-paraffins, one or more one-ring cycloparaffins, one or more multi-ring cycloparaffins, and one or more aromatic compounds, through a first separation unit comprising a first adsorbent material that is a metal organic framework selected from a zirconium, hafnium, cerium, or titanium-based metal organic framework, thereby selectively adsorbing the one or more one-ring cycloparaffins, the one or more multi-ring cycloparaffins, and the one or more aromatic compounds within the first adsorbent material; withdrawing from the first adsorbent material a first raffinate stream comprising less selectively adsorbed one or more n-paraffins and the one or more iso-paraffins; and withdrawing from the first adsorbent material a first extract stream comprising the selectively adsorbed one or more one-ring cycloparaffins, the one or more multi-ring cycloparaffins, and the one or more aromatic compounds, wherein the method is conducted in a liquid phase.

In some embodiments, the method further comprises the steps of: passing the first raffinate stream through a second separation unit with a second adsorbent material that is a medium pore zeolite, thereby selectively adsorbing one or more n-paraffins; withdrawing from the second adsorbent material a second extract stream comprising the selectively adsorbed one or more n-paraffins; and withdrawing from the second adsorbent material a second raffinate stream comprising the less selectively adsorbed one or more iso-paraffins.

In some embodiments, the method is performed in batch or continuous mode.

In another aspect, the advanced liquid phase adsorptive separation method of the present disclosure can be used for ternary separation of the components of a hydrocarbon mixture. In some embodiments, the feed stream comprising a hydrocarbon mixture is passed through a separation unit with an adsorbent material comprising a metal organic framework selected from a zirconium, hafnium, cerium, or titanium-based metal organic framework. In one embodiment, the metal organic framework is a zirconium-based metal organic framework. The feed stream is separated into classes of hydrocarbon compounds with a continuous cyclic bed, such as a simulated moving bed apparatus or a true moving bed apparatus (SMB/TMB). The method is conducted in a liquid phase. The SMB/TMB comprises a binary (two-product) or a ternary (three-product) outlet. The hydrocarbon mixture comprises one or more n-paraffins, one or more iso-paraffins, one or more one-ring cycloparaffins, one or more multi-ring cycloparaffins, and one or more aromatic compounds.

A SMB system can have several beds that, while fixed, alternate between an adsorption stage, a desorption stage, and optionally one or more purge stages. The ratio of beds operating in an adsorption stage can generally be equal to or less than the number of beds operating in a desorption or regeneration stage. In an embodiment, the ratio of beds in adsorption to desorption is between about 1:1 and 1:5, between about 1:1 and 1:4, between about 1:1 and 1:3, and between about 1:1 and 1:2. The SMB system can include a plurality of fixed sorbent beds, each sorbent bed including a sorbent, a first port at an end of the bed and a second port at an end of the bed distal to the first port; an adsorption stage and a desorption stage; and a series of valves and lines interconnecting each of the beds via the first and second ports. Examples of SMB systems are described in U.S. Pat. Nos. 2,985,589; 3,510,423; 3,686,342; and 5,750,820 and U.S. Patent Application Publication No. 2008/036913, each of which is incorporated herein by reference. Those of ordinary skill in the art are familiar with the design and operation of a SMB system.

Any conventional moving bed system could be used in lieu of a SMB system, including a vertical flowing moving bed and a circulating moving bed systems. The present technological advancement could be implemented using a combination of SMB and TMB. However, SMB technology can be preferred when separating complex mixtures into two streams where each stream including components having similar adsorptive properties (i.e., accounting for differences in pressure/temperature and/or other operational parameters, similarity can be assessed. Conventionally, SMBs utilized a concentration-based displacement by using a solvent. The solvent is distributed into the extract and the raffinate stream which often requires two distillation processes in the backend to recover the solvent from the two product streams. The extract is the slow moving/more adsorptive part of the feed—aromatics in this case, while the raffinate is the faster moving/less adsorptive part of the feed—saturates in this case. The solvent can be selected from the solvent-range saturates stream or solvent-range aromatics stream recycled from the backend membrane process.

In some embodiments, the metal organic framework adsorbent material preferentially adsorbs hydrocarbons in the order of the one or more one-ring cycloparaffins and the one or more multi-ring cycloparaffins, the one or more aromatics, the one or more iso-paraffins, followed by the one or more n-paraffins. In some embodiments, the metal organic framework adsorbent material preferentially adsorbs one or more aromatic compounds as strongly as or even more strongly than the one or more one-ring cycloparaffins and the one or more multi-ring cycloparaffins. Using this order of adsorption strength, one could use a single adsorptive separation unit with SMB/TMB to achieve ternary separation to isolate these differ hydrocarbons from a hydrocarbon mixture.

In some embodiments, the SMB/TMB comprises a ternary outlet and the method separates the feed stream into (a) a stream comprising the one or more n-paraffins, (b) a stream comprising the one or more iso-paraffins, and (c) a stream comprising the one or more one-ring cycloparaffins, the one or more multi-ring cycloparaffins, and the one or more aromatic compounds.

In some embodiments, the SMB/TMB comprises a binary outlet and the method separates the feed stream into (a) a stream comprising the one or more n-paraffins and the one or more iso-paraffins and (b) a stream comprising the one or more one-ring cycloparaffins, the one or more multi-ring cycloparaffins, and the one or more aromatic compounds.

In another aspect, the advanced liquid phase adsorptive separation method of the present disclosure is combined with refining and downstream processes. Distillation is typically the cornerstone of all current refining processes. Following distillation, a range of conversion processes change the size and structure of the hydrocarbon compounds. Some of the conversion processes and downstream processes include: Cracking, reforming, synthesis, treatment processes, and blending.

Steam or naphtha cracking—breaking down large molecules into smaller, mostly unsaturated hydrocarbon molecules with steam.

Reforming—rearranging molecules into different geometric structures such as in isomerization, dehydrogenation, dehydrocyclization, hydrocracking, and related processes. Reforming of the naphtha fraction is used to improve octane rating for gasoline and to provide aromatics for chemicals and generate hydrogen for refining treatment processes.

Synthesis—building smaller molecules into larger molecules such as in alkylation and oligomerization.

Treatment processes—preparing streams after pre-post distillation and conversion processes for additional processing and to prepare finished products. Often chemical and physical separation is utilized to meet the criteria. Processes include desalting, hydrodesulfurization, solvent treating/extraction, gas sweetening ($CO_2$ and $H_2S$ removal), and dewaxing.

Blending—mixing and combining hydrocarbon fractions with each other and/or additives to realize finished products with specific product specifications. Often this is the last step in refining.

In some embodiments, the liquid phase adsorptive separation method of the present invention further comprises the step of supplying the one or more extract streams and the one or more raffinate streams from the adsorptive separation process to a conversion unit or a blending unit. In some embodiments, a first extract stream or a first raffinate stream is supplied to a conversion unit and a second extract stream or a second raffinate stream is distilled prior to supplying to a conversion unit or a blending unit. In some embodiments, the conversion unit is selected from a cracking unit, a reforming unit, or a synthesis unit.

Figure 3:
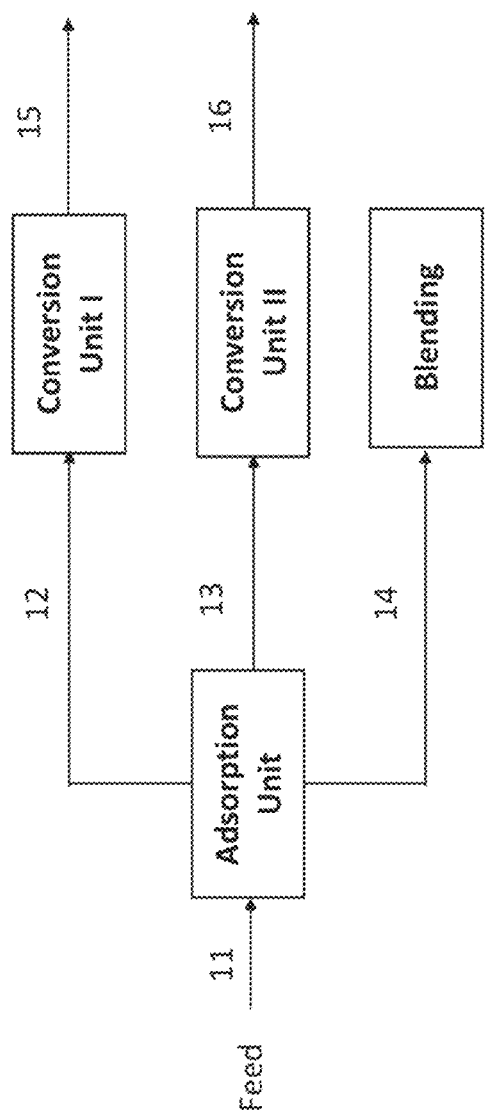
FIG. 3 is a flow diagram of a process for separating classes of hydrocarbon compounds from a feed stream in combination with refining and downstream processes according to one embodiment of the present disclosure.

One embodiment of the method for adsorptive molecular class separation of a feed stream in combination with refining and downstream processes is illustrated in FIG. 3, in which a feed stream comprising a hydrocarbon mixture is fed via line 11 to an "Adsorption Unit". The feed stream, which could be a fractional cut that may come from a main distillation tower of crude oil, comprises one or more n-paraffins, one or more iso-paraffins, one or more one-ring cycloparaffins, one or more multi-ring cycloparaffins, and one or more aromatic compounds. The Adsorption Unit comprises a plurality of separation units arranged in a series in any order. Each separation unit comprises a different adsorbent which preferentially adsorbs a different hydrocarbon compound. Separated streams with pure, substantially pure, or rich in each of the hydrocarbon classes exit the Adsorption Unit and are fed into different hydrocarbon conversion processes (labeled as "Conversion Unit I" and "Conversion Unit II") via line 12 and line 13 or they are fed into blending pools (such as, the unit labeled as "Blending") via line 14, depending on the desired target. The conversion unit can be, for example, a cracking unit, a reforming unit, a hydrotreating unit, or a synthesis unit. The streams with the end products of the conversion processes exit Conversion Unit I via line 15 and Conversion Unit II via line 16.

Figure 4:
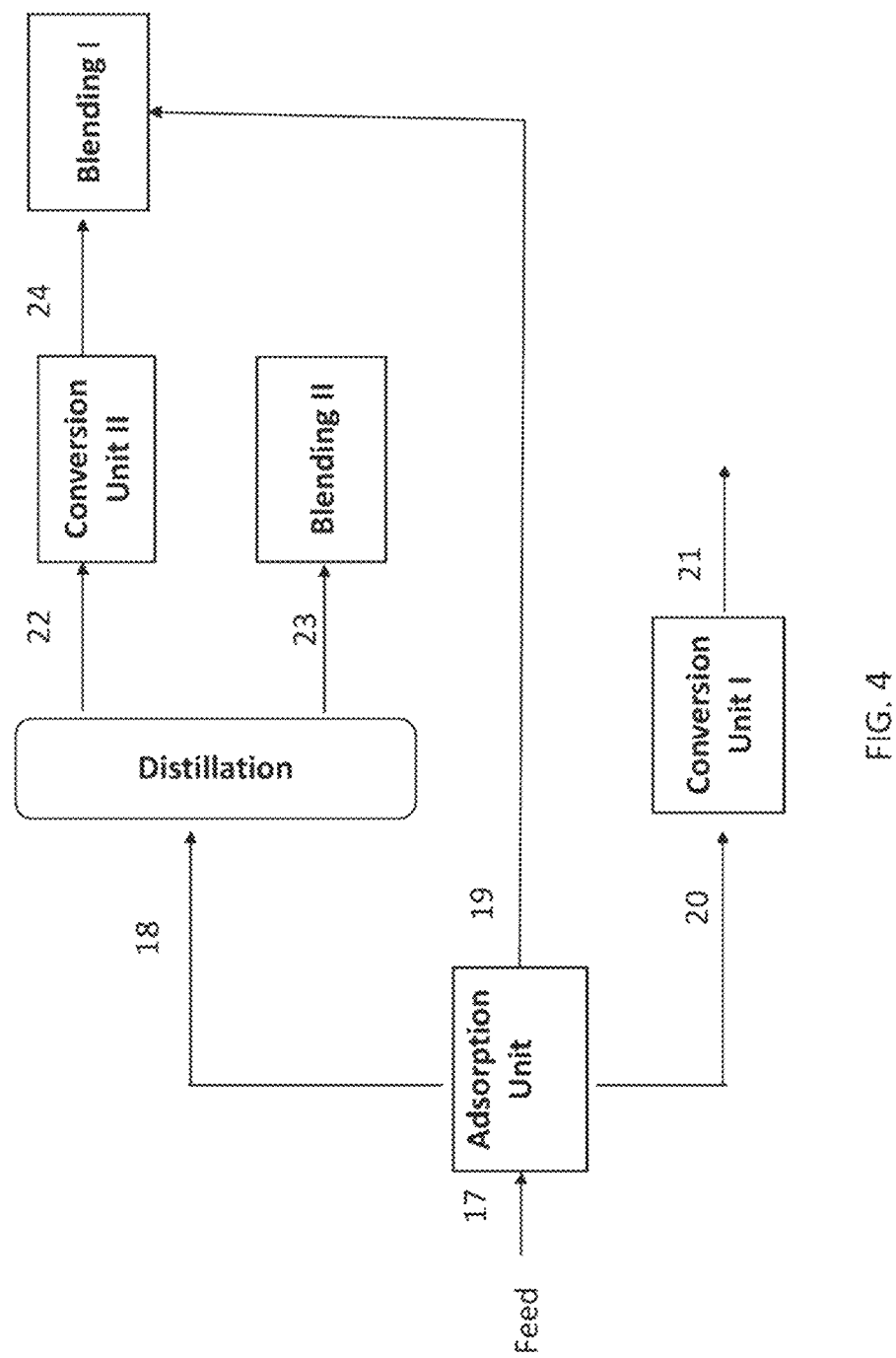
FIG. 4 is a flow diagram of a process for separating classes of hydrocarbon compounds from a feed stream in combination with refining and downstream processes according to one embodiment of the present disclosure.

Another embodiment of the method for adsorptive molecular class separation of a feed stream in combination with refining and downstream processes is illustrated in FIG. 4, where the feed stream comprising a hydrocarbon mixture is fed into an Adsorption Unit via line 17. The feed stream, which could be a fractional cut that may come from a main distillation tower of crude oil, comprises one or more n-paraffins, one or more iso-paraffins, one or more one-ring cycloparaffins, one or more multi-ring cycloparaffins, and one or more aromatic compounds. The Adsorption Unit comprises a plurality of separation units arranged in a series in any order. Each separation unit comprises a different adsorbent which preferentially adsorbs a different hydrocarbon compound. Separated streams with pure, substantially pure, or rich in each of the hydrocarbon classes exit the Adsorption Unit and are fed into various refining or downstream processes based on the desired target. In the illustrated embodiment of FIG. 4, the separated hydrocarbon streams are fed into a "Distillation" unit via line 18, a first blending unit labeled as "Blending Unit I" via line 19, or a first conversion unit labeled as "Conversion Unit I" via line 20. The stream with the end product of the conversion process exits Conversion Unit I via line 21. The different fractions of the distillation are removed and are either fed into a second conversion unit labeled as "Conversion Unit II" via line 22 or are fed into a second blending unit labeled as "Blending Unit II" via line 23. The stream with the end product of the conversion process exits Conversion Unit II via line 24 into the first Blending Unit I. Separating a feed stream by hydrocarbon class prior to feeding into conversion and downstream refining processes has several advantages. It could allow more efficient operation and/or optimization of downstream refining processes, such as catalytic reformers. For example, as noted above, without such a hydrocarbon class separation of the feed stream, paraffinic compounds in a reformer feed undergo cracking, which is one of undesired reactions occurring during reforming, as cracking compounds are primarily normal-paraffins and branched paraffins. In contrast, by separating a cycloparaffinic feed and providing a naphthenes only feed to a reformer will help reduce side reactions. Running naphthenic feed could also increase hydrogen production and reduce reforming severity by operating at lower temperatures without sacrificing product specification (i.e., octane number). It would also minimize downstream purification steps such as extraction to isolate aromatics from residual paraffins in the reformer products. In addition, for molecular upgrade to enhance octane rating, isomerization that is equilibrium limited reaction to convert normal to branched paraffins could benefit from separation of n-paraffins and mono-branched paraffins from multi-branched paraffins. The method to obtain hydrocarbon class separations of the present disclosure will therefore, enhance molecular management with significant value creation.

Illustrative embodiments of the separation process of the present disclosure are provided below to show some of the configurations of the separation units to provide the desired hydrocarbon class separation. In some embodiments, the configurations include a plurality of separation units, each separation unit having a different adsorbent material, connected in series to provide the desired adsorptive separation of classes of hydrocarbons from hydrocarbon mixtures. In other embodiments, the configurations include a single separation unit. It should be understood, however, that the invention is not limited to the specific details set forth in the illustrative configurations.

Illustrative Configuration 1

Figure 5:
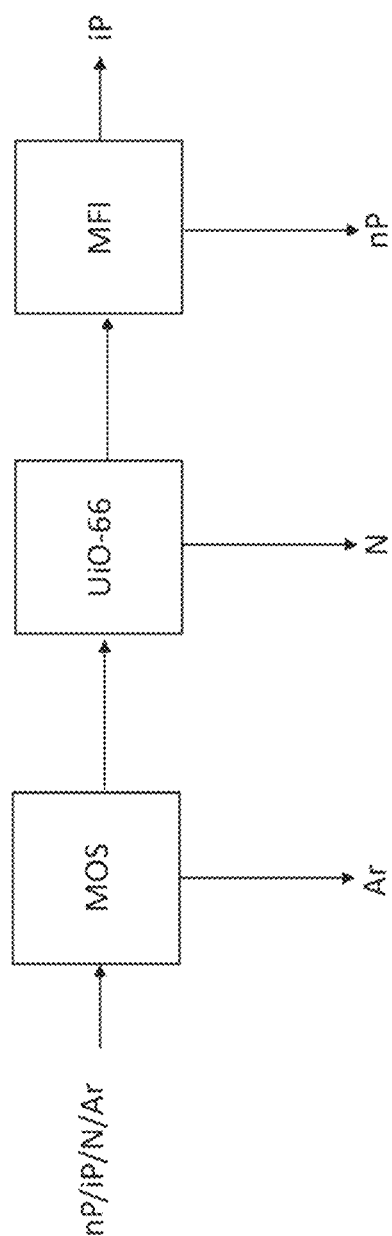
FIG. 5 is a flow diagram of a process for separating classes of hydrocarbon compounds from a feed stream according to one embodiment of the present disclosure.

Three separation units are configured in series as shown in FIG. 5. In this configuration, a feed stream comprising n-paraffins ("nP"), iso-paraffins ("iP"), one-ring cycloparaffins and multi-ring cycloparaffins (naphthenes "N"), and aromatic compounds ("Ar") is fed to a first separation unit with MOS adsorbent ("MOS"). MOS adsorbent preferentially adsorbs aromatics, which exit the MOS separation unit as a stream rich in aromatics. The remaining aromatic depleted stream, which comprises n-paraffins, iso-paraffins, and naphthenes, exits the MOS separation unit and is subsequently fed to a second separation unit with UiO-66 adsorbent ("UiO-66"). UiO-66 preferentially adsorbs naphthenes, which exit the UiO-66 separation unit as a stream rich in naphthenes. The remaining aromatic and naphthene depleted stream, which comprises n-paraffins and iso-paraffins, exits the UiO-66 separation unit and is subsequently fed to a third separation unit with MFI adsorbent ("MFI"). MFI adsorbent preferentially adsorbs n-paraffins, which exit the MFI separation unit as a stream rich in n-paraffins. The iso-paraffins exit the MFI separation unit as a raffinate stream.

Illustrative Configuration 2

Figure 6:
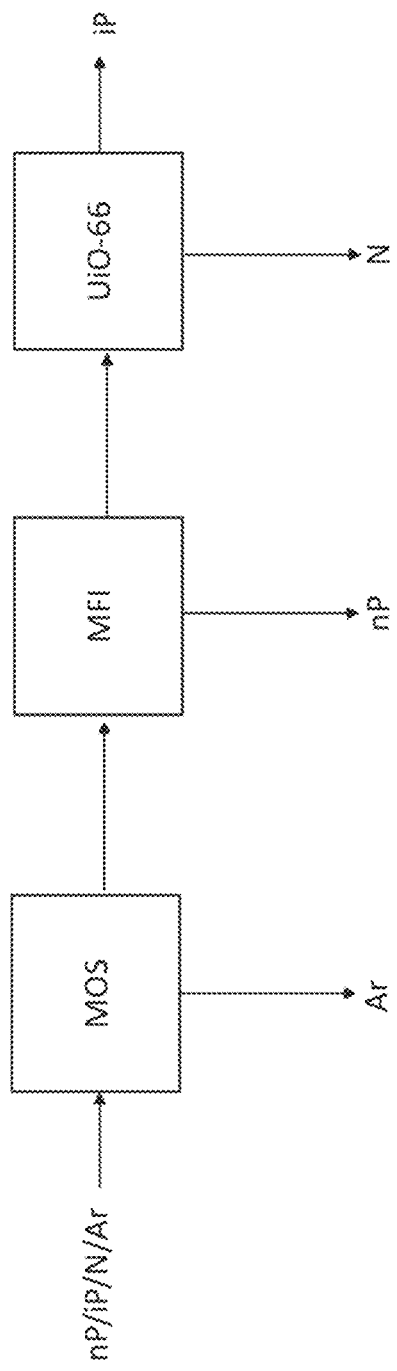
FIG. 6 is a flow diagram of a process for separating classes of hydrocarbon compounds from a feed stream according to one embodiment of the present disclosure.

Three separation units are configured in series as shown in FIG. 6. In this configuration, a feed stream comprising n-paraffins ("nP"), iso-paraffins ("iP"), one-ring cycloparaffins and multi-ring cycloparaffins (naphthenes "N"), and aromatic compounds ("Ar") is fed to a first separation unit with MOS adsorbent ("MOS"). MOS adsorbent preferentially adsorbs aromatics, which exit the MOS separation unit as a stream rich in aromatics. The remaining aromatic depleted stream, which comprises n-paraffins, iso-paraffins, and naphthenes, exits the MOS separation unit and is subsequently fed to a second separation unit with MFI adsorbent ("MFI"). MFI adsorbent preferentially adsorbs n-paraffins, which exit the MFI separation unit as a stream rich in n-paraffins. The remaining aromatic and n-paraffin depleted stream, which comprises naphthenes and iso-paraffins, exits the MFI separation unit and is subsequently fed to a third separation unit with UiO-66 adsorbent ("UiO-66"). UiO-66 preferentially adsorbs naphthenes, which exit the UiO-66 separation unit as a stream rich in naphthenes. The iso-paraffins exit the UiO-66 separation unit as a raffinate stream.

Illustrative Configuration 3

Figure 7:
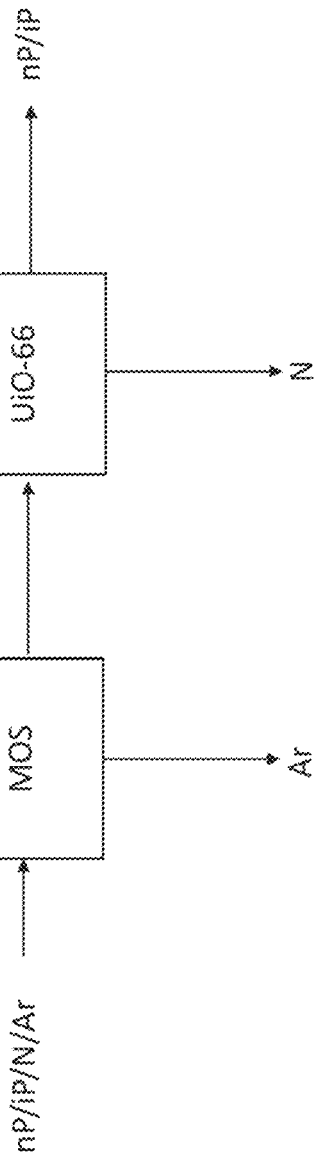
FIG. 7 is a flow diagram of a process for separating classes of hydrocarbon compounds from a feed stream according to one embodiment of the present disclosure.

Two separation units are configured in series as shown in FIG. 7. A binary SMB system can be used for such a configuration. In this configuration, a feed stream comprising n-paraffins ("nP"), iso-paraffins ("iP"), one-ring cycloparaffins and multi-ring cycloparaffins (naphthenes "N"), and aromatic compounds ("Ar") is fed to a first separation unit with MOS adsorbent ("MOS"). MOS adsorbent preferentially adsorbs aromatics, which exit the MOS separation unit as a stream rich in aromatics. The remaining aromatic depleted stream, which comprises n-paraffins, iso-paraffins, and naphthenes, exits the MOS separation unit and is subsequently fed to a second separation unit with UiO-66 adsorbent ("UiO-66"). UiO-66 preferentially adsorbs naphthenes, which exit the UiO-66 separation unit as a stream rich in naphthenes. The n-paraffins and the iso-paraffins exit the UiO-66 separation unit as a raffinate stream.

Illustrative Configuration 4

Figure 8:
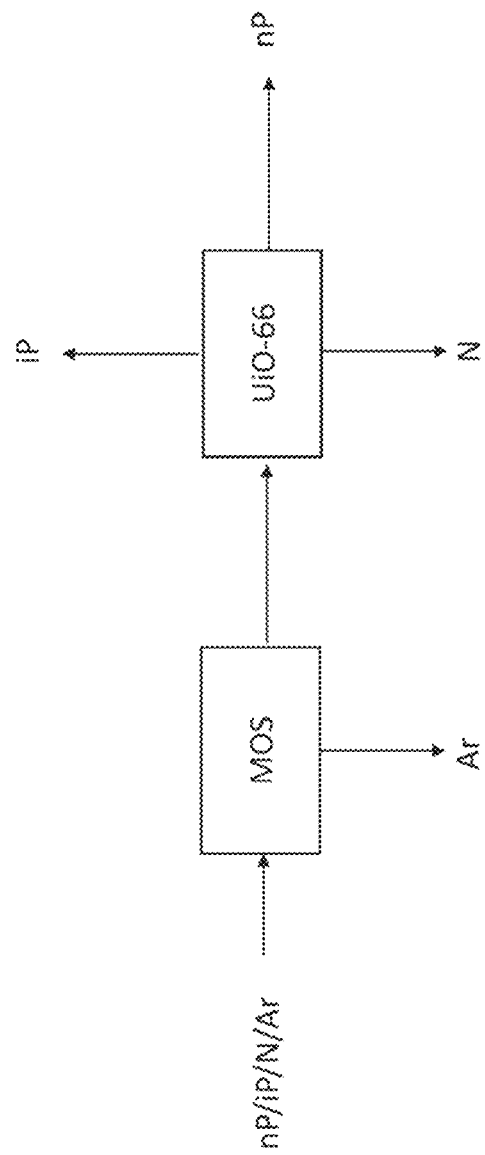
FIG. 8 is a flow diagram of a process for separating classes of hydrocarbon compounds from a feed stream according to one embodiment of the present disclosure.

Two separation units are configured in series as shown in FIG. 8. The hydrocarbon mixture in the feed stream, the first and the second adsorbent materials, and their order of placement are the same as in ILLUSTRATIVE CONFIGURATION 3 (as illustrated in FIG. 7). However, by using a ternary SMB system, in addition to the two extract streams rich in aromatics and naphthenes, respectively, as shown in FIG. 8, two other streams can be obtained that are rich in n-paraffins and iso-paraffins, respectively.

Illustrative Configuration 5

Figure 9:
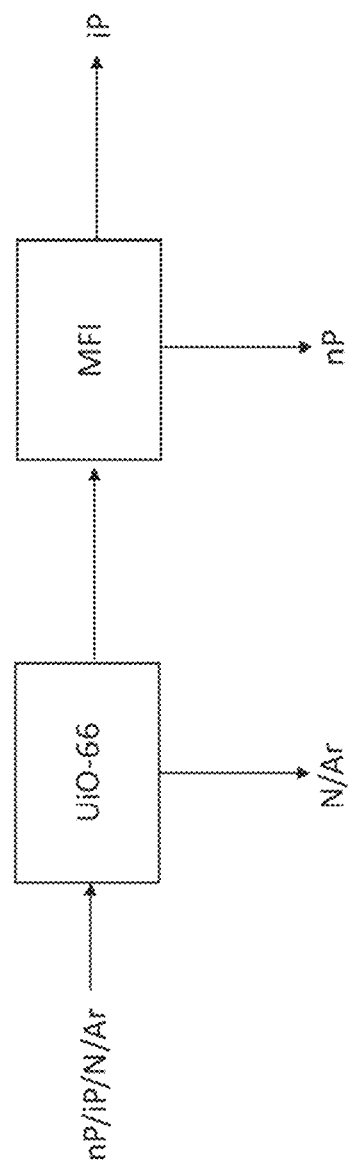
FIG. 9 is a flow diagram of a process for separating classes of hydrocarbon compounds from a feed stream according to one embodiment of the present disclosure.

Two separation units are configured in series as shown in FIG. 9. In this configuration, a feed stream comprising n-paraffins ("nP"), iso-paraffins ("iP"), one-ring cycloparaffins and multi-ring cycloparaffins (naphthenes "N"), and aromatic compounds ("Ar") is fed to a first separation unit with UiO-66 adsorbent ("UiO-66"). Such a configuration can be used, for example, when the concentration of the one or more aromatic compounds is low. In some embodiments, the concentration of the one or more aromatic compounds is less than 30 wt % of the feed stream. UiO-66 preferentially adsorbs both naphthenes and aromatics. The extract stream that exited the UiO-66 separation unit was a stream rich in naphthenes and aromatics. Since the concentration of aromatics in the initial feed is low in this configuration, separation of naphthenes and aromatics may not be necessary. The remaining naphthene and aromatic depleted stream, which comprises n-paraffins and iso-paraffins, exits the UiO-66 separation unit and is subsequently fed to a second separation unit with MFI adsorbent ("MFI"). MFI adsorbent preferentially adsorbs n-paraffins, which exit the MFI separation unit as a stream rich in n-paraffins. The remaining iso-paraffins exit the MFI separation unit as a raffinate stream.

Thus, the above examples show that depending on the relative concentrations of the hydrocarbon classes in the feed stream or on the compositions of the feed stream that are desired for subsequent downstream processes, it may be more efficient to design and optimize the process configurations to produce a stream of a particular hydrocarbon class (e.g., ILLUSTRATIVE CONFIGURATION 4) or a mixture stream of two hydrocarbon classes (e.g., ILLUSTRATIVE CONFIGURATION 5).

Illustrative Configuration 6

Figure 10:
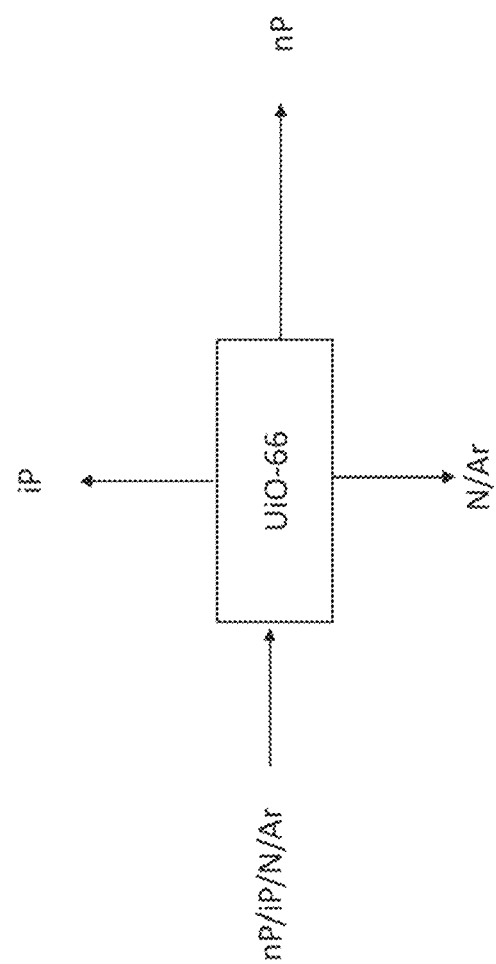
FIG. 10 is a flow diagram of a process for separating classes of hydrocarbon compounds from a feed stream according to one embodiment of the present disclosure.

A single separation unit with UiO-66 adsorbent ("UiO-66") can be used as shown in the configuration of FIG. 10. In this configuration, a feed stream comprising n-paraffins ("nP"), iso-paraffins ("iP"), one-ring cycloparaffins and multi-ring cycloparaffins (naphthenes "N"), and aromatic compounds ("Ar") is fed to the separation unit with UiO-66 adsorbent. This embodiment shows that using UiO-66 as adsorbent material that retains aromatic compounds, naphthenes, iso-paraffins, and n-paraffins in order of adsorption strength, one could use one adsorptive separation unit to achieve ternary separation to isolate n-paraffins in the raffinate, iso-paraffins in the first extract and a mixture of naphthenes and aromatic compounds in the secondary extract streams. UiO-66 offers this inverse selectivity compared to MFI, as it retains the iso-paraffins and naphthenes compared to MFI or LTA that retains n-paraffins. This unique selectivity also makes it a suitable adsorbent material for separating streams with the iso-paraffins and n-paraffins. The flexibility to isolate any of hydrocarbon class within the saturated compounds is possible when using this newly discovered separation technology based on UiO-66.

Illustrative Configuration 7

Figure 11:
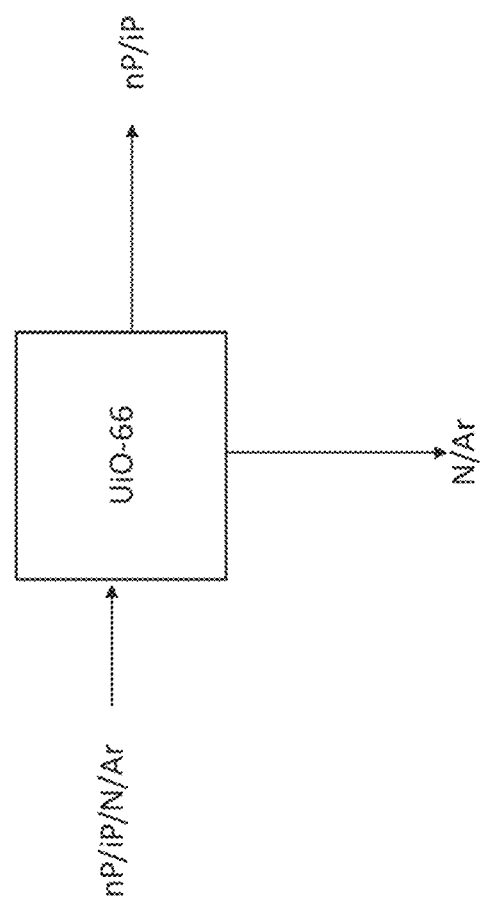
FIG. 11 is a flow diagram of a process for separating classes of hydrocarbon compounds from a feed stream according to one embodiment of the present disclosure.

Another embodiment with a single separation unit with UiO-66 adsorbent ("UiO-66") is shown in FIG. 11. In this configuration, a feed stream comprising n-paraffins ("nP"), iso-paraffins ("iP"), one-ring cycloparaffins and multi-ring cycloparaffins (naphthenes "N"), and aromatic compounds ("Ar") is fed to the separation unit with UiO-66 adsorbent. The resultant streams can be: (i) a stream rich in a mixture of the naphthenes and aromatics and (ii) a stream rich in a mixture of n-paraffins and iso-paraffins.

Illustrative Configuration 8

Figure 12:
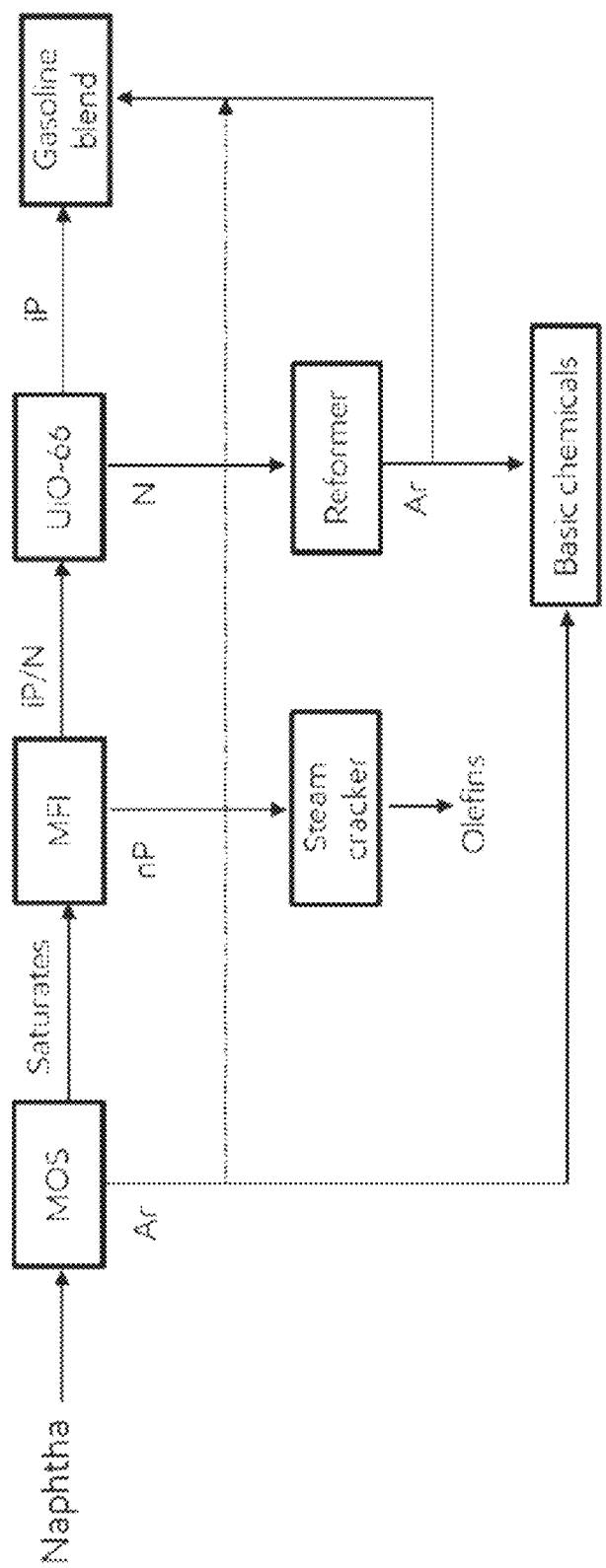
FIG. 12 depicts a flow diagram of a process for separating classes of hydrocarbon compounds from a feed stream in combination with refining and downstream processes according to one embodiment of the present disclosure.

FIG. 12 depicts a flow diagram of a process for separating classes of hydrocarbon compounds from a feed stream in combination with refining and downstream processes according to one embodiment of the present disclosure. In this embodiment of the present invention, naphtha feed streams (labeled as "Naphtha") are fed to the first separation unit to split into saturated compounds (labeled as "Saturates") and aromatic compounds (labeled as "Ar"). Non-limiting examples of saturated compounds include, for example, n-paraffins, iso-paraffins, and naphthenes. The adsorbent material in this step could be mesoporous organo silica (MOS), silica gel, or metal organic framework (MOF). As illustrated, the adsorbent material in the first separation unit is MOS. The isolated aromatics could be blended to gasoline pool as fuel or sent to further separation such as distillation for use as purified chemicals. The stream rich in the saturated compounds could be further separated into n-paraffins, naphthenes, and iso-paraffins using different microporous adsorbent materials in multiple subsequent adsorptive separation steps to produce advantaged feeds for conversion processes such as steam cracker, reformer or isomerization.

Illustrative Configuration 9

Figure 13:
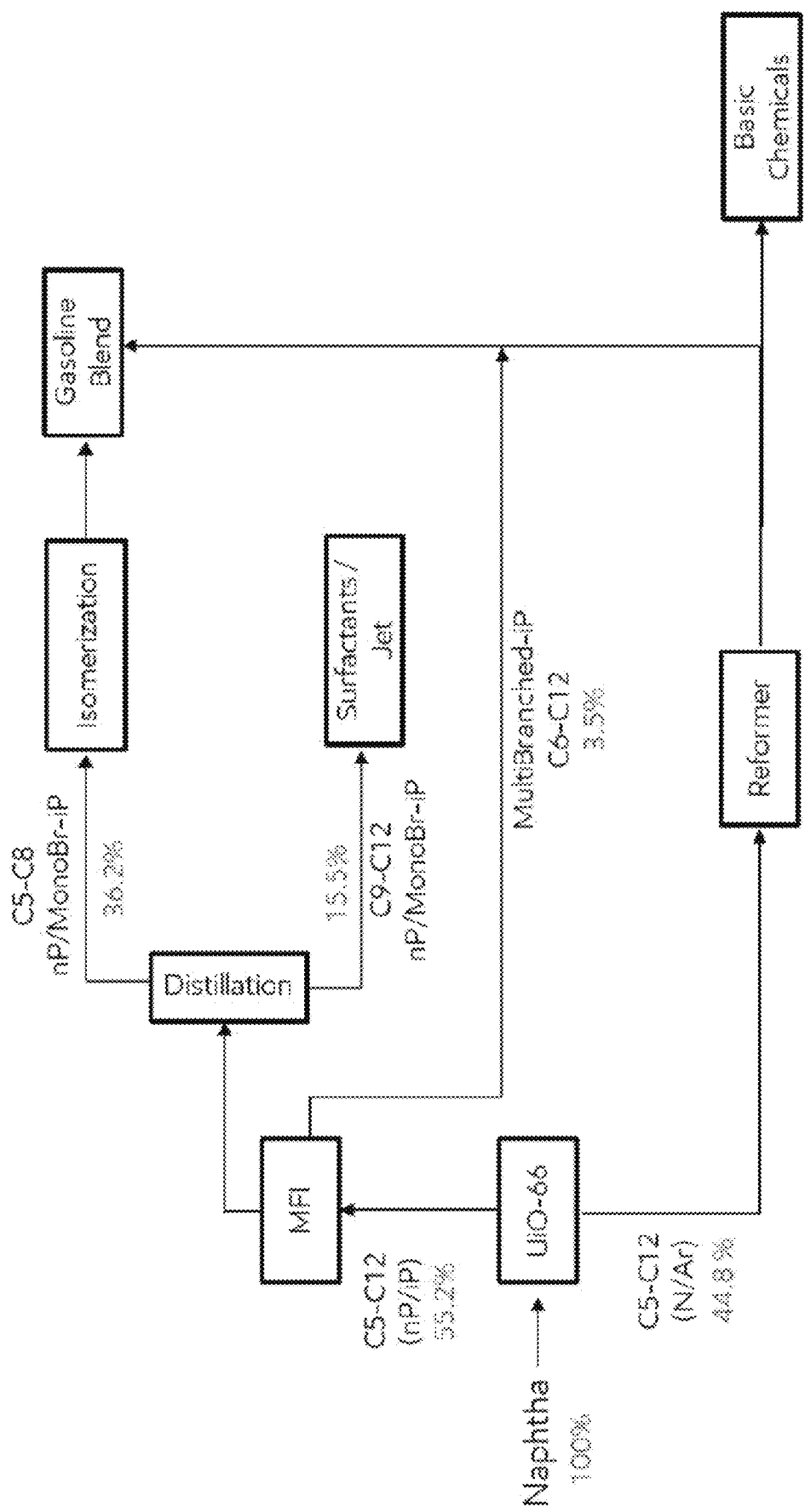
FIG. 13 depicts a flow diagram of a process for separating classes of hydrocarbon compounds from a feed stream in combination with refining and downstream processes according to one embodiment of the present disclosure. Volume % of each stream is included as an example.

FIG. 13 depicts a flow diagram of a process for separating classes of hydrocarbon compounds from a feed stream in combination with refining and downstream processes according to one embodiment of the present disclosure. Volume % of each stream is included as an example. In this configuration, naphtha feed streams are fed to the separation unit using UiO-66 adsorbent material for separation into two streams of naphthene plus aromatic compounds (labeled as "N/Ar") and n-paraffins plus iso-paraffins (labeled as "nP/iP"). The stream with N/Ar may be directly fed to a reformer for manufacturing of aromatics, whereas the other stream with nP/iP could be sent for further separation using MFI adsorbent to isolate multi-branched iso-paraffins (labeled as "Multibranched-iP") in one stream to enhance octane rating, while enriching more linear n-paraffins (labeled as "nP/MonoBr-iP") in the other stream in order to manufacture other chemicals (surfactants) or fuels (e.g., Jet). In other embodiments of the process of the present disclosure, depending on the composition of the feed stream and the capacity of adsorbent beds, the reverse configuration of UiO-66 and MFI separation steps could be applied.

The following examples are given as specific illustrations of the claimed invention. It should be understood, however, that the invention is not limited to the specific details set forth in the examples.

Example 1

A liquid chromatographic system was used for the breakthrough/pulse study of the adsorbents at elevated temperature. The adsorbents were pelleted, sized to 100-200 mesh and dry-packed into 4.6 mm ID×100 mm long stainless steel columns with 0.5 micron frits at each end. The adsorbent was dried at 150° C. for 2 hours in a flow of dry nitrogen. Prior to injection, the column was equilibrated at 150° C. with a solvent (i.e., desorbent). The solvents (i.e., desorbents) used were 2,2,4-trimethyl-pentane (iso-octane) and n-hexane. A synthetic hydrocarbon mixture solution was prepared using standard compounds, including n-heptane ("nC7"), n-octane ("nC8"), dodecane ("nC12"), isopentane ("iC5"), isooctane ("iC8"), 2-methylheptane ("2MC7"), 4-methylheptane ("4MC7"), 2,4-dimethylhexane ("2,4DMC6"), 2,5-dimethylhexane ("2,5DMC6"), cyclohexane ("CyC6"), methylcyclohexane ("MeCyC6"), cis-/trans-decalins ("DHNC/DHNT"). The mixture was introduced to the column through loop injection. The flow rate of solvent was set at 0.4 ml/min at an inlet pressure of about 50 bar. Effluent from the column was collected in the fraction collector and concentrations of each component in the fractions were analyzed by high resolution GC. Comprehensive Two-Dimensional Gas Chromatography (2DGC) was applied to characterize and obtain compositional information of naphtha cut from the refinery stream.

The adsorbents evaluated in the Examples were a Metal Organic Framework (MOF) (e.g., controlled defect ridden UiO-66 Zr-MOF, as discussed above ("UiO-66")), mesoporous organo silica ("MOS"), and the medium pore zeolite MFI ("MFI"). Table 1 below summarizes the characteristics of these adsorbents as well as for silica gel.

TABLE 1

| Adsorbent | Acronym | Surface Area ($m^2/g$) | Pore Size (Å) | Composition | Function |
|---|---|---|---|---|---|
| Silica Gel | SG | ~500 | 30 | $SiO_2$ | Aromatic adsorption |
| Mesoporous Organo Silica | MOS | ~1000 | 30 | —(Si—O—$CH_2$—)O— | Aromatic adsorption |
| Metal Organic Framework (MOF) | UiO-66 | ~1000 | 7 | $Zr_6(OH)_4O_4(BDC)_6$, where "BDC" is benzene-1,4-dicarboxylate | Aromatic or Naphthene adsorption |
| Zeolite, MFI | ZSM-5 | ~450 | 5.5 | $SiO_2/Al_2O_3$ > 1000 | n-Paraffin adsorption |

Example 2

Figure 14:
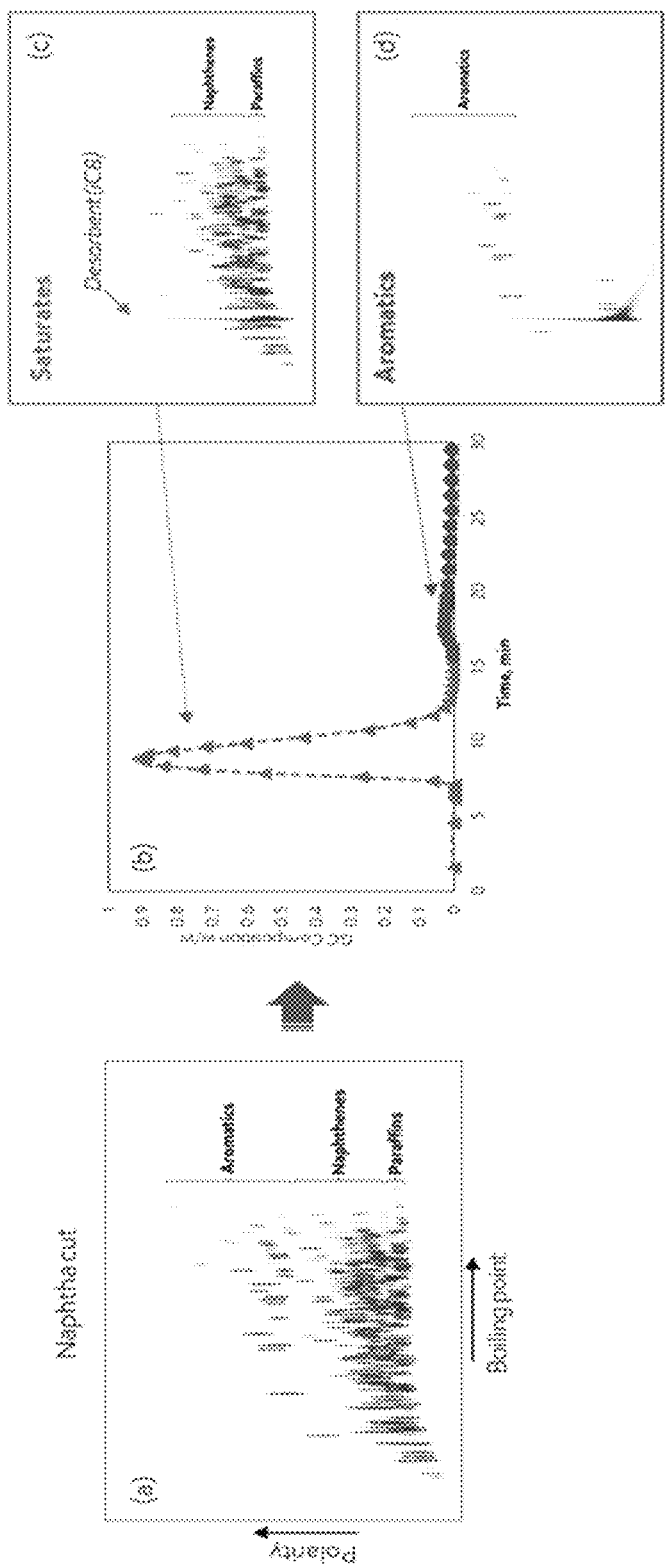
FIG. 14(*a*) depicts chromatogram obtained using two-dimensional gas chromatography (2DGC) of a feed composition.

FIGS. 14 (a)-(d) show aromatic compounds/saturated compounds separation using MOS as adsorbent material and naphtha cut as a feed stream. FIG. 14(a) depicts chromatogram obtained using two-dimensional gas chromatography (2DGC) of a feed composition comprising aromatic compounds, naphthenes and paraffins (n-paraffins and iso-paraffins). FIG. 14(b) depicts reconstructed chromatogram after running the feed composition of FIG. 14(a) through a packed bed of MOS. FIG. 14(c) depicts 2DGC chromatogram of one of the paraffin fractions obtained by the process of FIG. 14(b) and FIG. 14(d) depicts 2DGC chromatogram of one of the aromatic fractions obtained by the process of FIG. 14(b).

Detailed composition analysis by 2DGC indicates separation of the complex naphtha feed stream into two separate groups (i.e., aromatic compounds and saturated compounds). These chromatograms confirm that a separation unit with MOS as the adsorbent material preferentially adsorbs aromatic compounds from a hydrocarbon mixture compared to saturated compounds.

Example 3

Figure 15:
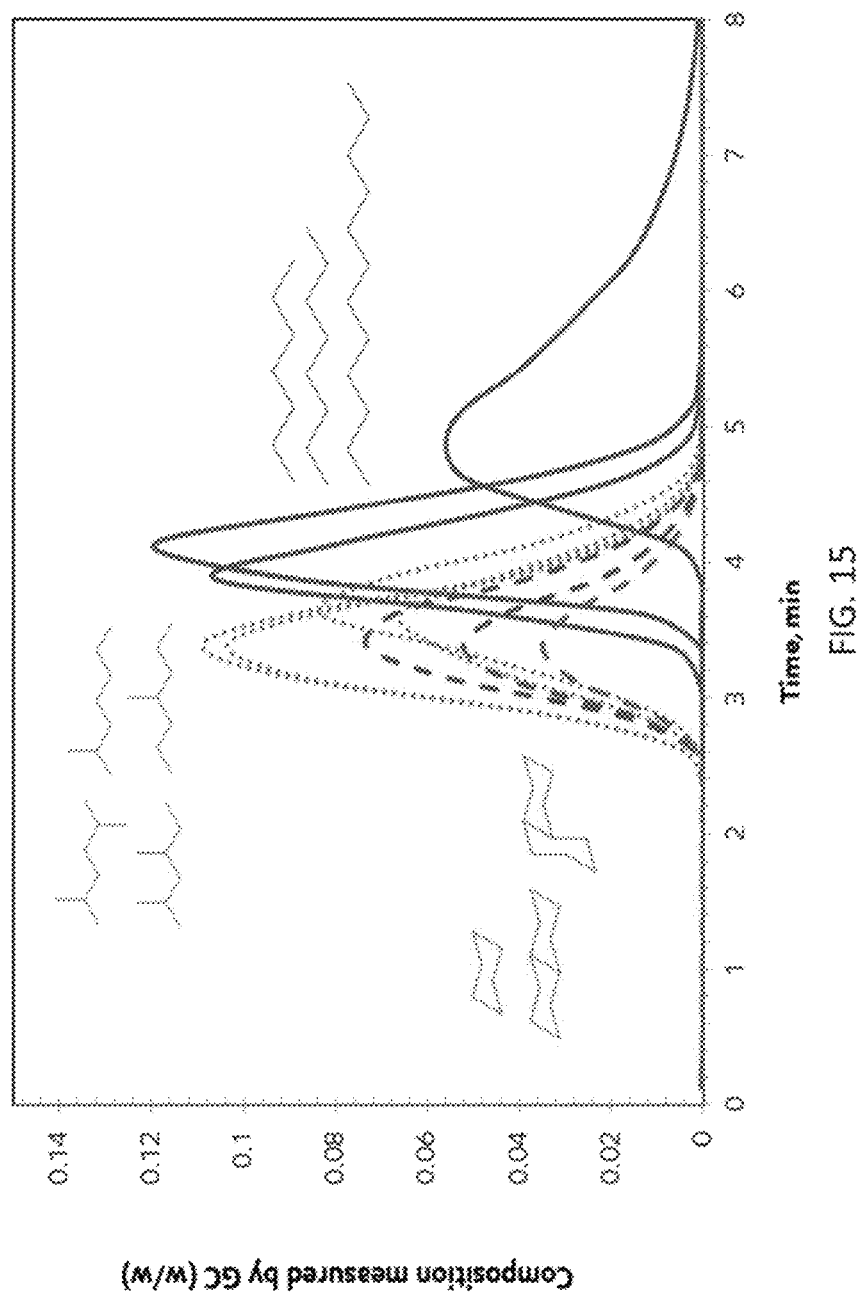
FIG. 15 depicts chromatographic traces for a pulse injection of a hydrocarbon mixture using MFI zeolite as adsorbent and n-hexane as desorbent at 150° C. according to one embodiment of the process of the present disclosure. The chromatogram for n-paraffins is depicted as solid lines, for iso-paraffins as dotted lines, and for naphthenes as dashed lines.

In this example, the pulse experiment under the same conditions as for EXAMPLE 1 was performed. FIG. 15 depicts chromatographic traces for a pulse injection of a hydrocarbon mixture using microcrystalline silica MFI zeolite (ZSM-5) as adsorbent and n-hexane as desorbent at 150° C. according to one embodiment of the process of the present disclosure. The chromatogram for n-paraffins is depicted as solid lines, for iso-paraffins as dotted lines, and for naphthenes as dashed lines. These chromatograms confirm that a separation unit with MFI zeolite as the adsorbent material preferentially adsorbs n-paraffins from a hydrocarbon mixture.

Example 4

Figure 16:
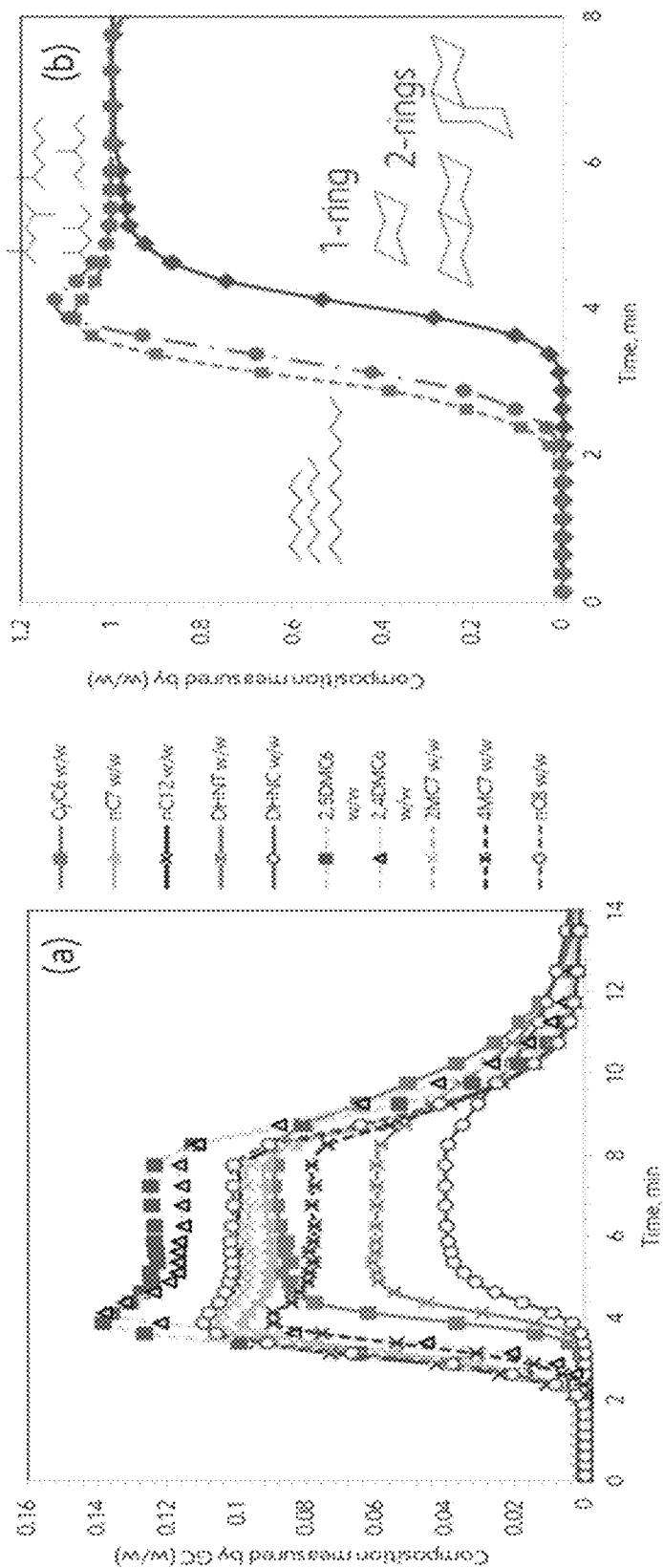
FIG. 16 depicts breakthrough curves for a hydrocarbon mixture using a controlled defect ridden UiO-66 Zr-MOF as adsorbent and n-hexane as solvent at 150° C. in two different formats.

In this example, the pulse experiment under the same conditions as for EXAMPLE 1 was performed. FIG. 16 depicts breakthrough curves for a hydrocarbon mixture using a controlled defect ridden UiO-66 Zr-MOF as adsorbent and n-hexane as solvent at 150° C. in two different formats: FIG. 16(*a*) depicts overlays of individual breakthrough curves of components; FIG. 16(*b*) depicts overlays of breakthrough curves by a compound class (normalized by each component's initial concentration).

These results confirm that a separation unit with a controlled defect ridden UiO-66 Zr-MOF as the adsorbent material preferentially adsorbs naphthenes, including both one and multi-rings naphthenes, from a hydrocarbon mixture. As illustrated in FIG. 16(*b*), first breakthrough profile with roll-up of n-paraffins indicates weakest adsorption of n-paraffins, being displaced by iso-paraffins, which is then displaced by 1-ring and 2-ring naphthenes. These results illustrate that a controlled defect ridden UiO-66 Zr-MOF adsorbent material is capable of the separating n-paraffins, iso-paraffins, and naphthenes in a ternary adsorptive separation scheme. Because UiO-66 Zr-MOF adsorbent material separates n-paraffins from the hydrocarbon mixture, it can be used to achieve the same molecular class-based separation without the use of MFI based separation that offers n-paraffins isolation from the hydrocarbon mixture.

Example 5

Figure 17:
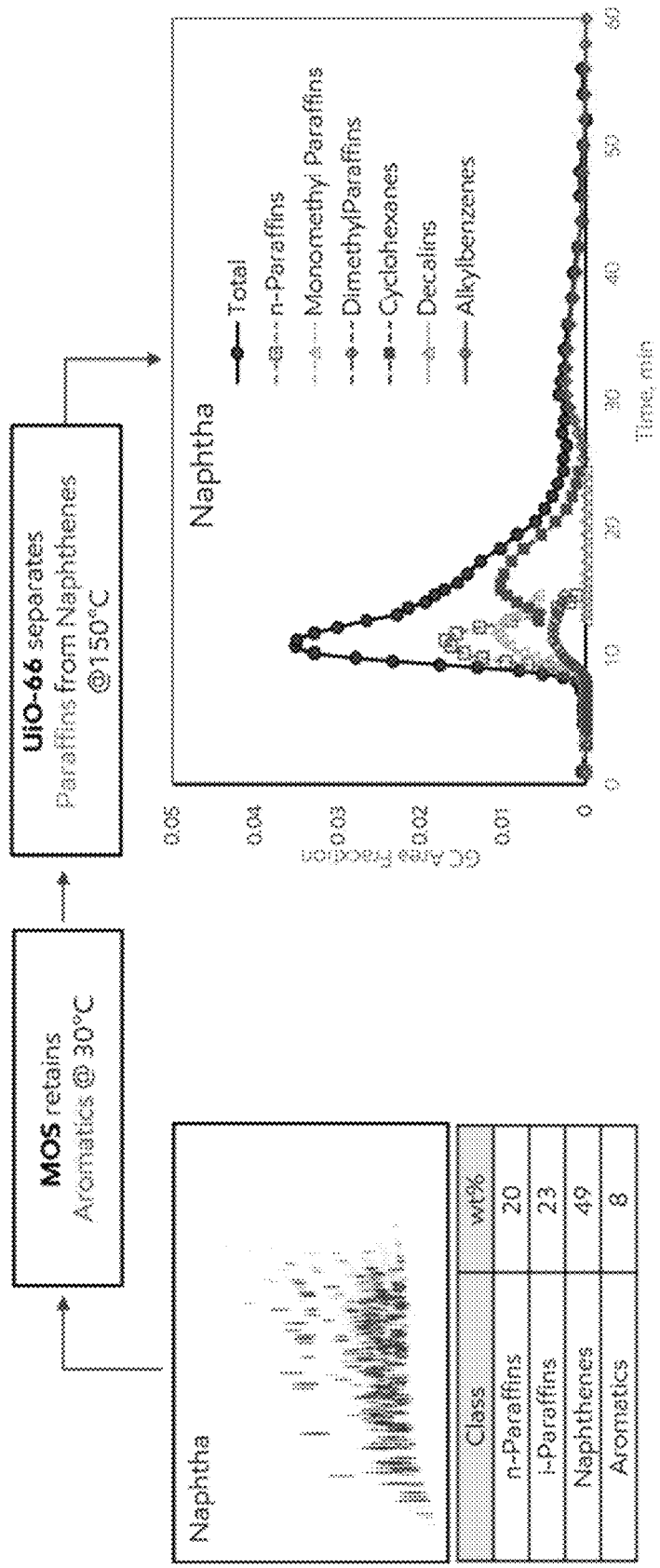
FIG. 17 depicts on the left side 2DGC chromatogram of a feed composition and, on the right side, it depicts reconstructed chromatogram after running the feed composition shown on the left side through a packed bed of mesoporous organo silica (MOS) followed by a packed bed of a controlled defect ridden UiO-66 Zr-MOF.

This example describes the use of two different adsorbent materials (mesoporous organo silica (MOS) followed by a packed bed of a controlled defect ridden UiO-66 Zr-MOF) connected in series to demonstrate paraffins, naphthenes and aromatic separation. The naphtha cut feed stream was fed to the two beds in liquid phase. Paraffins eluted first, followed by naphthenes and aromatics. Separation gained from the first bed (i.e., MOS) was maintained after adding the second bed (i.e., UiO-66) because the second bed retains naphthenes and aromatics more strongly than paraffins. FIG. 17 depicts on the left side 2DGC chromatogram of a feed composition and, on the right side, it depicts reconstructed chromatogram after running the feed composition shown on the left side through a packed bed of mesoporous organo silica (MOS) followed by a packed bed of UiO-66.

These results confirm that a combination of two separation units (each with a different adsorbent material) in series results in true molecular class separation of naphtha cut feed stream. In particular, the separation unit with the MOS adsorbent material preferentially adsorbs aromatic compounds from a hydrocarbon mixture, while the UiO-66 adsorbent material preferentially adsorbs naphthene from a hydrocarbon mixture.

Example 6

Figure 18:
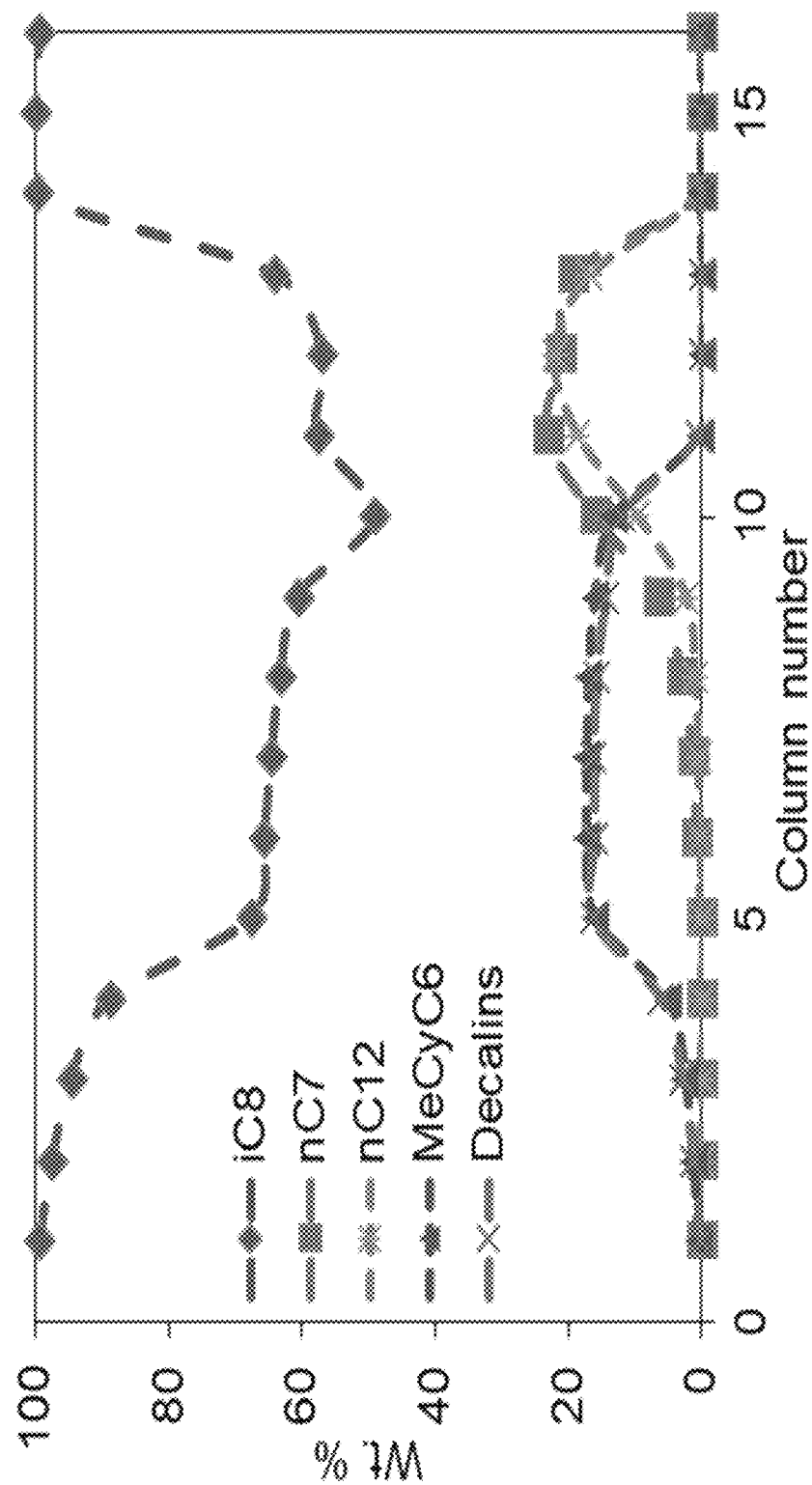
FIG. 18 depicts Simulated Moving Bed (SMB) run of a hydrocarbon mixture according to one embodiment of the present disclosure.

In this SMB experiment shown in FIG. 18, UiO-66 was used as the adsorbent material and isooctane (iC8) was used as the desorbent at 150° C. The adsorbent was packed in 16 beds (~6.9 g of 100-200 mesh particles of UiO-66 per 16.1 cc size of a bed) that were configured for the experiment. The flow rates of desorbent, extract, raffinate and recycle were 1.93, 1.2, 0.5, 1.23 and 5.07 ml/min, respectively, with a switching time of 1.9 minutes. As a result of the continuous adsorptive separation process, the extract stream had 99%+ solvent-free purities of both the naphthenes (methylcyclohexane (MeCyC6)+decalins) and the raffinate stream had 99%+ solvent-free purities of both the paraffins (n-heptane (nC7)+n-dodecane (nC12)). This SMB experiment uses isooctane (iC8) as desorbent, which overlaps with naphtha range molecules in terms of a boiling point, thereby making difficult to recover desorbent simply by distillation.

Table 2 below shows the purity of the feed, extract and raffinate from the SMB experiment.

TABLE 2

| Purity wt % | Feed | Extract | Raffinate |
| --- | --- | --- | --- |
| MeCyC6 | 25 | 99+ | <1 |
| Decalins | 25 | 99+ | <1 |
| nC7 | 25 | <1 | 99+ |
| nC12 | 25 | <1 | 99+ |

Example 7

Figure 19:
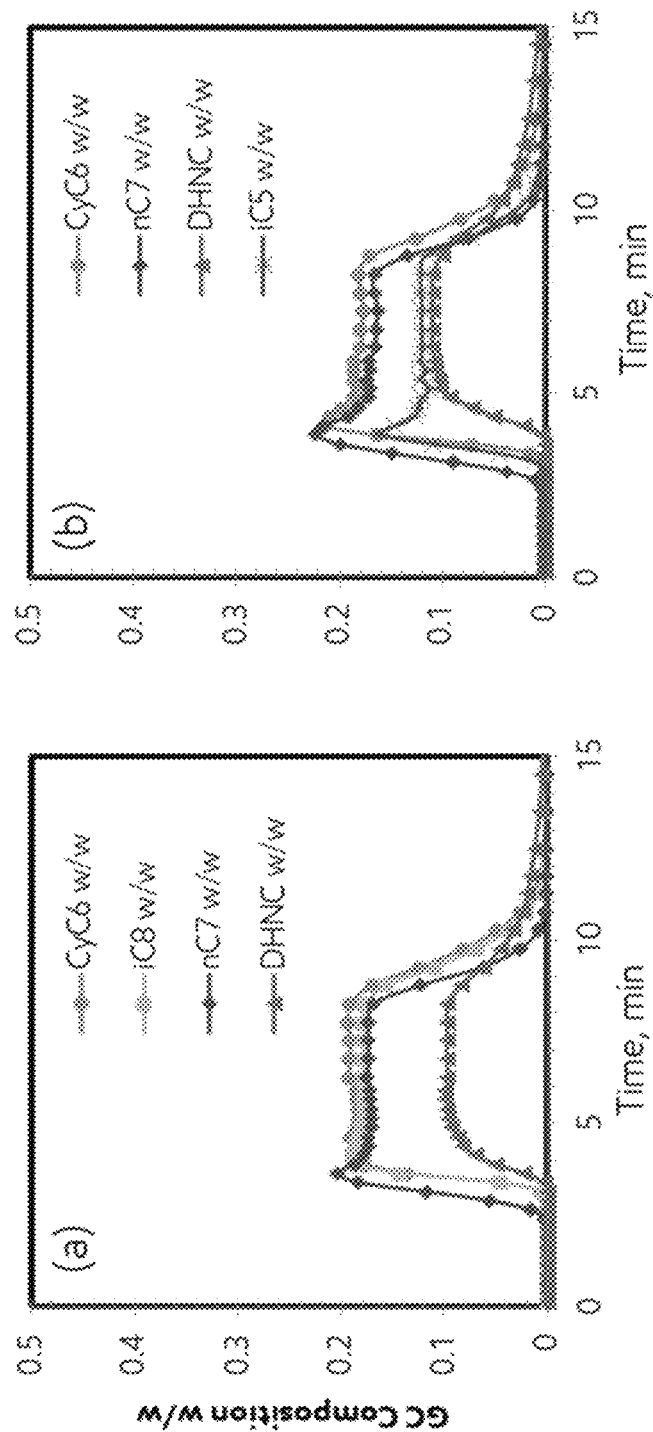
FIG. 19 depicts breakthrough curves using a controlled defect ridden UiO-66 Zr-MOF as adsorbent and n-hexane as solvent at 150° C. for: a mixture with isooctane (iC8) (FIG. 19(*a*)) and a mixture with isopentane (iC5) (FIG. 19(*b*)).

Desorbent selection is an important part of the overall adsorptive separation process. Light hydrocarbons such as C5 or lower can be used to facilitate subsequent desorbent recovery process. In this example, the breakthrough experiment under the same conditions as for EXAMPLE 1 was performed to compare the adsorption strength of isooctane (iC8) and isopentane (iC5). FIG. 19 depicts breakthrough curves using a controlled defect ridden UiO-66 Zr-MOF as adsorbent and n-hexane as solvent at 150° C. for: a mixture with isooctane (iC8) (FIG. 19(*a*)) and a mixture with isopentane (iC5) (FIG. 19(*b*)). These results show that isopentane (iC5), which has much lower boiling point than most of naphtha range molecules, can be used as desorbent because it exhibits adsorption strength similar to that of isooctane (iC8).

Below are embodiments of the invention:

Embodiment A: A method for separating classes of hydrocarbon compounds from a feed stream, the method comprising the steps of:
  passing a feed stream comprising a hydrocarbon mixture through a plurality of separation units arranged in a series in any order, wherein each separation unit has an adsorbent material; and
  separating classes of hydrocarbon compounds from the feed stream,
  wherein one of the plurality of separation units comprises an adsorbent material that is a metal organic framework selected from a zirconium, hafnium, cerium, or titanium-based metal organic framework;
  wherein another of the plurality of separation units has an adsorption material that is different from the metal organic framework; and
  wherein the method is conducted in a liquid phase.

Embodiment B: The method of Embodiment A, wherein the another of the plurality of separation units comprises an adsorbent material that is independently selected from a porous silica, a small pore zeolite, a medium pore zeolite, or a large pore zeolite.

Embodiment C: The method of Embodiment B, wherein the porous silica is silica gel, mesoporous organo silica, or clay.

Embodiment D: The method of Embodiment B, wherein the large pore zeolite has a 12 membered or larger ring structure.

Embodiment E: The method of Embodiment B, wherein the large pore zeolite is selected from MWW (MCM-22), MOR (Mordenite), FAU (zeolite 13X, zeolite X, zeolite Y, Siliceous Y), EMT (ZSM-3), MAS (ZSM-4), MTW (ZSM-12), MEI (ZSM-18), EMT (ZSM-20), BEA (Beta), LTL (zeolite L), or DON (UTD-1).

Embodiment F: The method of Embodiment B, wherein the small pore zeolite has an 8 membered ring structure and the medium pore zeolite has a 10 membered ring structure.

Embodiment G: The method of Embodiment B, wherein the small pore zeolite is selected from LTA (ZK-4, zeolite A), or KFI (ZK-5), zeolite A, or zeolite T, and the medium pore zeolite is selected from MFI (ZSM-5), MEL (ZSM-11), TON (ZSM-22), MTT (ZSM-23), FER (ZSM-35), or MRE (ZSM-48).

Embodiment H: The method of Embodiment B, wherein the hydrocarbon mixture comprises one or more n-paraffins, one or more iso-paraffins, one or more one-ring cycloparaffins, one or more multi-ring cycloparaffins, and one or more aromatic compounds.

Embodiment I: The method of Embodiment H, wherein the feed stream is a refinery stream.

Embodiment J: The method of Embodiment H, wherein the separation unit comprising an adsorbent material that is the porous silica or the large pore zeolite generates an extract stream comprising the one or more aromatic compounds.

Embodiment K: The method of Embodiment H, wherein the separation unit comprising an adsorbent material that is the metal organic framework generates an extract stream comprising the one or more one-ring cycloparaffins and the one or more multi-ring cycloparaffins.

Embodiment L: The method of Embodiment H, wherein the separation unit comprising an adsorbent material that is the small pore zeolite or the medium pore zeolite generates an extract stream comprising the one or more n-paraffins.

Embodiment M: The method of Embodiment H, wherein the another of the plurality of separation units comprises in any order a first separation unit comprising an adsorbent material that is the porous silica and a second separation unit comprising an adsorbent material that is the small pore zeolite or the medium pore zeolite.

Embodiment N: The method of Embodiment M, wherein the method separates the feed stream in any order into (a) a stream comprising the one or more n-paraffins, (b) a stream comprising the one or more iso-paraffins, (c) a stream comprising the one or more one-ring cycloparaffins and the one or more multi-ring cycloparaffins, and (d) a stream comprising the one or more aromatic compounds.

Embodiment O: The method of Embodiment M, wherein the separation unit comprising an adsorbent material that is the metal organic framework generates an extract stream comprising the one or more one-ring cycloparaffins and the one or more multi-ring cycloparaffins, the separation unit comprising an adsorbent material that is the porous silica generates an extract stream comprising the one or more aromatic compounds, and the separation unit comprising an adsorbent material that is the small pore zeolite or the medium pore zeolite generates an extract stream comprising the one or more n-paraffins.

Embodiment P: The method of Embodiment H, wherein the another of the plurality of separation units comprises an adsorbent material that is the porous silica or the large pore zeolite.

Embodiment Q: The method of Embodiment P, wherein the method separates the feed stream in any order into (a) a stream comprising the one or more one-ring cycloparaffins and the one or more multi-ring cycloparaffins, (b) a stream comprising the one or more aromatic compounds, and (c) a stream comprising the one or more n-paraffins and (d) a stream comprising the one or more iso-paraffins.

Embodiment R: The method of Embodiment P, wherein the method separates the feed stream in any order into (a) a stream comprising the one or more one-ring cycloparaffins and the one or more multi-ring cycloparaffins, (b) a stream comprising the one or more aromatic compounds, and (c) a stream comprising the one or more n-paraffins and the one or more iso-paraffins.

Embodiment S: The method of Embodiment H, wherein the another of the plurality of separation units comprises an adsorbent material that is the small pore zeolite or the medium pore zeolite.

Embodiment T: The method of Embodiment S, wherein the method separates the feed stream in any order into (a) a stream comprising the one or more n-paraffins, (b) a stream comprising the one or more one-ring cycloparaffins, the one or more multi-ring cycloparaffins, and the one or more aromatic compounds, and (c) a stream comprising the one or more iso-paraffins.

Embodiment U: The method of Embodiment A, wherein each of the plurality of separation units is independently selected from a fixed bed apparatus, a moving bed apparatus, a simulated moving bed apparatus, a temperature swing adsorption apparatus, or a concentration swing adsorption apparatus.

Embodiment V: The method of Embodiment A, further comprising desorbing using at least one solvent.

Embodiment W: The method of Embodiment V, wherein the solvent comprises a saturated hydrocarbon, an aromatic hydrocarbon, or mixtures thereof.

Embodiment X: The method of Embodiment V, wherein the solvent is iso-octane, $C_4$-$C_8$ n-paraffin, hexane, cyclohexane, toluene, benzene, $CO_2$, ammonia, or mixtures thereof.

Embodiment Y: The method of claim 8, 9, 14, 15, 17, 18, or 20, wherein the one or more multi-ring cycloparaffins comprise one or more two-ring cycloparaffins.

Embodiment Z: The method of Embodiment Y, wherein the one or more one-ring cycloparaffins comprise one or more cyclohexanes, and one or more two-ring cycloparaffins comprise one or more decalins.

Embodiment A': The method of Embodiment A, wherein the method is performed between about 1 bar to about 100 bar.

Embodiment B': The method of Embodiment A, wherein the method is performed between about 25° C. and about 250° C.

Embodiment C': The method of Embodiment A, wherein the metal organic framework is a zirconium-based metal organic framework.

Embodiment D': The method of claim Embodiment C', wherein the zirconium-based metal organic framework exhibits an X-ray diffraction pattern containing peaks at d-spacings of about 11.98 Å, 10.37 Å, 7.32 Å, 6.24 Å, 5.98 Å, and 5.18 Å.

Embodiment E': The method of Embodiment C', wherein the zirconium-based metal organic framework comprises $Zr_6O_{32}$ clusters bridged by polytopic, carboxylate-based linkers.

Embodiment F': The method of Embodiment C', wherein the zirconium-based metal organic framework comprises a micropore volume, as measured by N2 adsorption at 77 K, greater than 0.38 cc/g.

Embodiment G': The method of Embodiment C', wherein the zirconium-based metal organic framework comprises a residual inorganic mass after combustion of the zirconium-based metal organic framework that is greater than about 45% of dry weight of zirconium-based metal organic framework measured at 300° C.

Embodiment H': The method of Embodiment C', wherein the zirconium-based metal organic framework can be represented by a general formula $Zr_6O_4(OH)_4BDC_{(6-x)}$, wherein BDC refers to benzene-1,4-dicarboxylate, and wherein x is greater than 0.5 as determined by residual inorganic mass after combustion.

Embodiment I': The method of Embodiment A, wherein the adsorbent material of the one of the plurality of separation units comprises about 90% metal organic framework and about 10% binder.

Embodiment J': The method of Embodiment A, wherein the method is performed in batch or continuous mode.

Embodiment K': The method of Embodiment H, further comprising:
generating:
one or more extract streams, wherein each extract stream comprises a class of hydrocarbon compounds from the feed stream, and
one or more raffinate streams comprising the rest of the classes of hydrocarbon compounds from the feed stream.

Embodiment L' The method of Embodiment K' further comprising:
supplying the one or more extract streams and the one or more raffinate streams to a conversion unit or a blending unit.

Embodiment M' The method of Embodiment L', wherein a first extract stream or a first raffinate stream is supplied to a conversion unit and a second extract stream or a second raffinate stream is distilled prior to supplying to a conversion unit or a blending unit.

Embodiment N': The method of Embodiment L', wherein the conversion unit is selected from a cracking unit, a reforming unit, or a synthesis unit.

Embodiment O': A method for separating classes of hydrocarbon compounds from a feed stream, the method comprising the steps of:
passing a feed stream comprising a hydrocarbon mixture through a separation unit with an adsorbent material comprising a metal organic framework selected from a zirconium, hafnium, cerium, or titanium-based metal organic framework; and
separating with a simulated moving bed apparatus or a true moving bed apparatus (SMB/TMB) classes of hydrocarbon compounds from the feed stream,
wherein the method is conducted in a liquid phase.

Embodiment P': The method of Embodiment O', wherein the SMB/TMB comprises a binary or a ternary outlet.

Embodiment Q': The method of Embodiment P', wherein the hydrocarbon mixture comprises one or more n-paraffins, one or more iso-paraffins, one or more one-ring cycloparaffins, one or more multi-ring cycloparaffins, and one or more aromatic compounds.

Embodiment R': The method of Embodiment Q', wherein the SMB/TMB comprises a ternary outlet and the method separates the feed stream into (a) a stream comprising the one or more n-paraffins, (b) a stream comprising the one or more iso-paraffins, and (c) a stream comprising the one or more one-ring cycloparaffins, the one or more multi-ring cycloparaffins, and the one or more aromatic compounds.

Embodiment S': The method of Embodiment Q', wherein the SMB/TMB comprises a binary outlet and the method separates the feed stream into (a) a stream comprising the one or more n-paraffins and the one or more iso-paraffins and (b) a stream comprising the one or more one-ring cycloparaffins, the one or more multi-ring cycloparaffins, and the one or more aromatic compounds.

Embodiment T': The method of Embodiment R' or Embodiment 5', wherein the metal organic framework is a zirconium-based metal organic framework.

Embodiment U': A method for separating classes of hydrocarbon compounds from a feed stream, the method comprising the steps of:
passing a feed stream comprising one or more n-paraffins, one or more iso-paraffins, one or more one-ring cycloparaffins, one or more multi-ring cycloparaffins, and one or more aromatic compounds, through a first separation unit comprising a first adsorbent material that is a metal organic framework selected from a zirconium, hafnium, cerium, or titanium-based metal organic framework,
thereby adsorbing the one or more one-ring cycloparaffins, the one or more multi-ring cycloparaffins, and the one or more aromatic compounds within the first adsorbent material; and
withdrawing from the first adsorbent material a first raffinate stream comprising the one or more n-paraffins and the one or more iso-paraffins; and
withdrawing from the first adsorbent material a first extract stream comprising the adsorbed one or more one-ring cycloparaffins, the one or more multi-ring cycloparaffins, and the one or more aromatic compounds,
wherein the method is conducted in a liquid phase.

Embodiment V': The method of Embodiment U', further comprising the steps of:
passing the first raffinate stream through a second separation unit with a second adsorbent material that is a medium pore zeolite, thereby adsorbing one or more n-paraffins;
withdrawing from the second adsorbent material a second extract stream comprising the adsorbed one or more n-paraffins; and
withdrawing from the second adsorbent material a second raffinate stream comprising the one or more iso-paraffins.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for separating classes of hydrocarbon compounds from a feed stream, the method comprising the steps of:
passing a feed stream comprising a hydrocarbon mixture through a plurality of separation units, the hydrocarbon mixture comprising one or more n-paraffins, one or more iso-paraffins, one or more one-ring cycloparaffins, one or more multi-ring cycloparaffins, and one or more aromatic compounds, wherein each separation unit has a different adsorbent material; and separating classes of hydrocarbon compounds from the feed stream, wherein a first separation unit comprises a metal organic framework selected from the group consisting of a zirconium-, hafnium-, cerium-, and titanium-based metal organic framework and generates an extract stream comprising the one or more one-ring cycloparaffins and the one or more multi-ring cycloparaffins;

wherein a second separation unit comprises an adsorbent material selected from the group consisting of a porous silica, a small pore zeolite, a medium pore zeolite, and a large pore zeolite;

wherein the method is conducted in a liquid phase; and wherein the plurality of separation units are arranged in a series in any order.

2. The method of claim 1, wherein the porous silica is silica gel, mesoporous organo silica, or clay.

3. The method of claim 1, wherein the large pore zeolite has a 12 membered or larger ring structure.

4. The method of claim 1, wherein the large pore zeolite comprises a framework selected from the group consisting of MWW, MOR, FAU, EMT, MAS, MTW, MEI, EMT, BEA, LTL, and DON.

5. The method of claim 1, wherein the small pore zeolite has an 8 membered ring structure and the medium pore zeolite has a 10 membered ring structure.

6. The method of claim 1, wherein the small pore zeolite comprises a framework selected from the group consisting of LTA, KFI, and ERI, and the medium pore zeolite comprises a framework selected from the group consisting of MFI, MEL, TON, MTT, FER, and MRE.

7. The method of claim 1, wherein the feed stream is a refinery stream.

8. The method of claim 1, wherein the second separation unit comprises the porous silica or the large pore zeolite and generates an extract stream comprising the one or more aromatic compounds.

9. The method of claim 1, wherein the second separation unit comprises the small pore zeolite or the medium pore zeolite and generates an extract stream comprising the one or more n-paraffins.

10. The method of claim 1, wherein the second separation unit comprises the porous silica, and wherein a third separation unit comprises the small pore zeolite or the medium pore zeolite.

11. The method of claim 10, wherein the method separates the feed stream in any order into (a) a stream comprising the one or more n-paraffins, (b) a stream comprising the one or more iso-paraffins, (c) a stream comprising the one or more one-ring cycloparaffins and the one or more multi-ring cycloparaffins, and (d) a stream comprising the one or more aromatic compounds.

12. The method of claim 10, wherein the second separation unit comprising the porous silica generates an extract stream comprising the one or more aromatic compounds, and the third separation unit comprising the small pore zeolite or the medium pore zeolite generates an extract stream comprising the one or more n-paraffins.

13. The method of claim 1, wherein the second separation unit comprises the porous silica or the large pore zeolite.

14. The method of claim 13, wherein the method separates the feed stream in any order into (a) a stream comprising the one or more one-ring cycloparaffins and the one or more multi-ring cycloparaffins, (b) a stream comprising the one or more aromatic compounds, and (c) a stream comprising the one or more n-paraffins and the one or more iso-paraffins.

15. The method of claim 1, wherein the second separation unit comprises the small pore zeolite or the medium pore zeolite.

16. The method of claim 15, wherein the method separates the feed stream in any order into (a) a stream comprising the one or more n-paraffins, (b) a stream comprising the one or more one-ring cycloparaffins, the one or more multi-ring cycloparaffins, and the one or more aromatic compounds, and (c) a stream comprising the one or more iso-paraffins.

17. The method of claim 1, wherein each of the plurality of separation units is independently selected from the group consisting of a fixed bed apparatus, a moving bed apparatus, a simulated moving bed apparatus, a temperature swing adsorption apparatus, and a concentration swing adsorption apparatus.

18. The method of claim 1, further comprising desorbing a hydrocarbon compound from an adsorbent material using at least one solvent.

19. The method of claim 18, wherein the at least one solvent comprises a saturated hydrocarbon, an aromatic hydrocarbon, or mixtures thereof.

20. The method of claim 18, wherein the at least one solvent is iso-octane, $C_4$-$C_8$ n-paraffin, hexane, cyclohexane, toluene, benzene, $CO_2$, ammonia, or mixtures thereof.

21. The method of claim 1, wherein the one or more multi-ring cycloparaffins comprise one or more two-ring cycloparaffins.

22. A method for separating classes of hydrocarbon compounds from a feed stream, the method comprising the steps of:

passing a feed stream comprising a hydrocarbon mixture through a plurality of separation units, the hydrocarbon mixture comprising one or more n-paraffins, one or more iso-paraffins, one or more one-ring cycloparaffins, one or more multi-ring cycloparaffins, and one or more aromatic compounds, wherein each separation unit has a different adsorbent material; and separating classes of hydrocarbon compounds from the feed stream, wherein a first separation unit comprises a metal organic framework selected from the group consisting of a zirconium, hafnium, cerium, and titanium-based metal organic framework and generates an extract stream comprising the one or more one-ring cycloparaffins and the one or more multi-ring cycloparaffins;

wherein a second separation unit comprises a porous silica;

wherein a third separation unit comprises a small pore zeolite or a medium pore zeolite;

wherein the method is conducted in a liquid phase, and wherein the plurality of separation units are arranged in a series in any order.

23. The method of claim 22, wherein the method separates the feed stream in any order into (a) a stream comprising the one or more one-ring cycloparaffins and the one or more multi-ring cycloparaffins, (b) a stream comprising the one or more aromatic compounds, and (c) a stream comprising the one or more n-paraffins and (d) a stream comprising the one or more iso-paraffins.

* * * * *